(12) United States Patent
Perrow et al.

(10) Patent No.: US 12,403,222 B2
(45) Date of Patent: Sep. 2, 2025

(54) IMPLANTABLE DEVICE AND A METHOD FOR IMPLANTING SAID DEVICE IN A SUBJECT

(71) Applicant: UNIVERSITY OF WOLLONGONG, New South Wales (AU)

(72) Inventors: Kara Lea Perrow, Kembla Heights (AU); Samantha Jane Wade, Farmborough Heights (AU); Simon Edward Moulton, Northcote (AU); Sepehr Talebian, Wollongong (AU); Javad Foroughi, Mount Pleasant (AU); Morteza Aghmesheh, Austinmer (AU); Gordon George Wallace, Gwynneville (AU)

(73) Assignee: UNIVERSITY OF WOLLONGONG, New South Wales (AU)

( * ) Notice: Subject to any disclaimer, the term of this patent is extended or adjusted under 35 U.S.C. 154(b) by 1140 days.

(21) Appl. No.: 17/277,952

(22) PCT Filed: Sep. 23, 2019

(86) PCT No.: PCT/AU2019/051017
§ 371 (c)(1),
(2) Date: Mar. 19, 2021

(87) PCT Pub. No.: WO2020/056467
PCT Pub. Date: Mar. 26, 2020

(65) Prior Publication Data
US 2022/0118160 A1  Apr. 21, 2022

(30) Foreign Application Priority Data
Sep. 23, 2018  (AU) .................. 2018903570

(51) Int. Cl.
*A61L 29/04* (2006.01)
*A61K 31/337* (2006.01)
(Continued)

(52) U.S. Cl.
CPC .......... *A61L 29/049* (2013.01); *A61K 31/337* (2013.01); *A61K 31/7068* (2013.01);
(Continued)

(58) Field of Classification Search
None
See application file for complete search history.

(56) References Cited

U.S. PATENT DOCUMENTS

2008/0220054 A1   9/2008  Shastri et al.
2012/0089122 A1*  4/2012  Lee .................. A61L 29/16
                                              604/517

FOREIGN PATENT DOCUMENTS

CN   103046158 A   4/2013
CN   104264469 A   1/2015
(Continued)

OTHER PUBLICATIONS

Wade et al. "Preparation and in vitro assessment of wet-spun gemcitabine-loaded polymeric fibers: Towards localized drug delivery for the treatment of pancreatic cancer" Pancreatology. 1-10. (Year: 2017).*
(Continued)

*Primary Examiner* — Nicole P Babson
(74) *Attorney, Agent, or Firm* — Norris McLaughlin, PA

(57) ABSTRACT

Described is an implantable device and methods for preparing and implanting the device into a subject for use in treating a medical condition when implanted therein. The device comprises at least one coaxial fibre of a hydrophilic polymer and a hydrophobic polymer, wherein at least one of
(Continued)

said polymers is loaded with an agent that is active towards treating the medical condition.

17 Claims, 20 Drawing Sheets

(51) Int. Cl.
    *A61K 31/7068*     (2006.01)
    *A61L 29/16*     (2006.01)
    *A61M 25/00*     (2006.01)
    *A61M 25/01*     (2006.01)
    *D01D 5/06*     (2006.01)
    *D01D 5/34*     (2006.01)

(52) U.S. Cl.
    CPC ......... *A61L 29/16* (2013.01); *A61M 25/0023* (2013.01); *A61M 25/0108* (2013.01); *D01D 5/06* (2013.01); *D01D 5/34* (2013.01); *A61L 2300/216* (2013.01); *A61L 2300/232* (2013.01); *A61M 2210/1042* (2013.01)

(56) References Cited

FOREIGN PATENT DOCUMENTS

| | | |
|---|---|---|
| WO | 2004026111 A2 | 4/2004 |
| WO | 2008020931 A2 | 2/2008 |
| WO | 2014018563 A2 | 1/2014 |
| WO | 2015191547 A1 | 12/2015 |
| WO | 2018017929 A1 | 1/2018 |

OTHER PUBLICATIONS

Iqbal S, Rashid MH, Arbab AS, Khan M. "Encapsulation of Anticancer Drugs (5-Fluorouracil and Paclitaxel) into Polycaprolactone (PCL) Nanofibers and In Vitro Testing for Sustained and Targeted Therapy". J Biomed Nanotechnol. Apr.;13(4):355-366. (Year: 2017).*
Colomer R. Gemcitabine in combination with paclitaxel for the treatment of metastatic breast cancer. Womens Health (Lond). Nov.;1(3):323-9. (Year: 2005).*
International Search Report for corresponding application PCT/AU2019/051017 dated Oct. 21, 2019.
Deng-Guang Yu, et al: "Nanofibers Fabricated Using Triaxial Electrospinning as Zero Order Drug Delivery Systems", Applied Materials & Interfaces, vol. 7, No. 33, Aug. 26, 2015, pp. 18891-18897.
EP Search Report for corresponding application EP 19861987 dated Jun. 8, 2022.
SETA: "Development and Characterisation of Novel Coaxial Biopolymer Fibres", Master of Philosophy thesis, Intelligent Polymer Research Institute, University of Wollongong, 2016. [online] https://ro.uow.edu.au/theses/4969 (retrieved Oct. 10, 2019), pp. 1-90.
Xia et al.: Localized Controlled Delivery of Gemcitabine via Microsol Flectrospun Fibers to Prevent Pancreatic Cancer Recurrence, Advanced Healthcare Materials, Jul. 2018, vol. 7, article 1800593, pp. 1-13.

* cited by examiner

IMPLANTABLE DEVICE AND A METHOD FOR IMPLANTING SAID DEVICE IN A SUBJECT

TECHNICAL FIELD

The present invention relates to an implantable device and a method for implanting said device in a subject for use in treating a medical condition.

The invention has been developed primarily for use in treating subjects presenting with cancerous tumours and will be described hereinafter with reference to this application. However, it will be appreciated that the invention is not limited to this particular medical condition, and that the implantable device may be useful in treating other medical conditions.

The following discussion of the background to the invention is intended to facilitate an understanding of the invention. However, it should be appreciated that the discussion is not an acknowledgement or admission that any of the material referred to was published, known or part of the common general knowledge in Australia or any other country as at the priority date of any one of the claims of this specification.

BACKGROUND OF INVENTION

In spite of remarkable improvements in cancer treatments and survivorship, cancer still remains one of the major causes of death worldwide. Although current standards of care provide encouraging results, they still cause severe systemic toxicity and also fail in preventing recurrence of the disease.

For instance, pancreatic cancer has a dismal prognosis, with surgical resection in conjunction with systemic chemotherapy, the only potential curative therapy. Around 80% of diagnosed cases however are deemed unresectable prompting the need for the development of alternative treatment approaches.

The pancreatic tumour microenvironment is one of the biggest barriers facing current treatments.

Desmoplasia surrounding pancreatic tumours is one of the hallmarks of pancreatic ductal adenocarcinoma (PDAC). When compared to other solid tumours, PDAC demonstrates an increase in extracellular matrix proteins, for example collagen, as well as cytokines, chemokines and growth factors, all of which are produced by pancreatic stellate cells[3]. These proteins contribute to the desmoplasia, forming a fibrous stroma with high interstitial fluid pressure and low vascularity. Systemic delivery of chemotherapeutics is therefore impeded, and often results in high levels of systemic toxicity, which leads to cessation of treatment and tumour progression. Similarly, immunotherapy has failed to show any response in pancreatic cancer, despite huge success in other solid tumours such as melanoma, head and neck squamous cell carcinoma, kidney and bladder cancers.

Delivery of chemotherapy locally and in high doses is an effective way to relieve patients of the negative side effects of toxic chemotherapy, while still actively treating a cancerous tumour. There is also an opportunity to deliver targeted agents and immunotherapy drugs such as checkpoint inhibitors and vaccines directly into the pancreatic tumour using this technology. There are few publications describing implantable chemotherapy devices for PDAC.

In order to address these issues, biomaterial-based implantable drug delivery systems (DDSs) have emerged as promising therapeutic platforms that allow local administration of drugs directly to the tumour site. These DDSs are intended to enhance drug uptake and efficacy since they can be delivered locally (directly at the site of the tumour) and therefore offer strategic and precise spatial control to significantly reduce the required drug dosage and often the side/off-target effects, while presenting temporal control over the release profile of the drugs to maintain therapeutic concentrations over a longer duration of time, and protect the loaded drugs from degradation or clearance until they are released.

For instance, Indolfi et al., describes a stainless steel disk that is coated with a PLGA matrix containing paclitaxel, designed to be sutured to the outside surface of a pancreatic tumour[1]. Similarly, Yi et al., fabricated 3D printed patches comprised of a mixture of PLGA and PCL loaded with 5-fluorouracil[2]. In these instances, the patches are flexible and designed to be placed over the pancreatic tumour. However, a noted drawback using such patches is the toxicity toward normal, non-malignant cells outside the tumour after implantation. Additionally, the patch needs to be inserted surgically which is invasive.

The present invention seeks to provide an implantable device and a method for implanting said device in a subject for use in treating a medical condition, which will overcome or substantially ameliorate at least some of the deficiencies of the prior art, or to at least provide an alternative.

SUMMARY OF INVENTION

According to a first aspect of the present invention there is provided an implantable device for use in treating a medical condition when implanted into a subject, the device comprising: at least one coaxial fibre of a hydrophilic polymer and a hydrophobic polymer, wherein at least one of said polymers is loaded with an agent that is active towards treating the medical condition.

In one embodiment, the hydrophilic polymer corresponds to a core of the coaxial fibre and the hydrophobic polymer corresponds to a shell that surrounds the hydrophilic polymer core of the coaxial fibre.

In one embodiment, the hydrophobic polymer corresponds to a core of the coaxial fibre and the hydrophilic polymer corresponds to a shell that surrounds the hydrophobic polymer core of the coaxial fibre.

In one embodiment, the coaxial fibre is formed using a technique selected from the group consisting of wet spinning, electrospinning, coaxial melt extrusion printing, coaxial melt electro-writing, hot melt extrusion and pulsatile fibre spinning.

In one embodiment, the coaxial fibre is formed using a wet spinning technique.

In one embodiment, the hydrophobic polymer is selected from the group consisting of polycaprolactone, poly(lactic acid), poly(lactic-co-glycolic acid), poly(2-oxazoline), polyglycerol sebacate, poly(propylene glycol) and a poly(l-amino acid).

In one embodiment, the hydrophilic polymer is selected from the group consisting of alginate, chitosan, carboxymethyl cellulose, poly(vinyl alcohol), hyaluronic acid and poly(ethylene glycol).

In one embodiment, the hydrophobic polymer is polycaprolactone and the hydrophilic polymer is alginate.

In one embodiment, the coaxial fibre is produced by spinning a polymer dope comprising from about 15% to 20% polycaprolactone by weight/volume in solution, and about 3% to 5% alginate by weight/volume.

In one embodiment, the coaxial fibre is produced by spinning a polymer dope comprising from about 0.05% to about 0.1% polycaprolactone by weight, and about 0.9% to about 0.95% alginate by weight relative to the polycaprolactone.

Preferably, each of said hydrophilic polymer and said hydrophobic polymer is loaded with an agent that is active towards treating the medical condition.

Suitably, the active agent is selected from the group consisting of: a chemotherapeutic agent, a biologic, an immune modulating agent, a radioactive or radioisotope material, a contrast agent, a fluorescent dye, a steroid, a fatty acid, a vitamin, and any combination thereof.

Suitably, the active agent is a hydrophobic drug loaded into the hydrophobic polymer.

In one embodiment, the hydrophobic drug is selected from the group consisting of paclitaxel, camptothecan, everolimus, epothilone, curcumin, docetaxel, and any combination thereof.

Suitably, the active agent is a hydrophilic drug loaded into the hydrophilic polymer.

In one embodiment, the hydrophilic drug is selected from the group consisting of: gemcitabine, nivolumab, a platinum agent, 5-fluorouracil, irinotecan, a taxane, cyclophosphamide, rituximab, cetuximab, trastuzumab, pertuzumab, sunitinib, bevacizumab, an anti-EGFR molecule, an anti-CTLA4 antibody, an anti-PD1 or anti-PDL1 antibody or inhibitor, tisagenlecleucel, an immune modulating agent, and any combination thereof.

In one embodiment, the medical condition to be treated is cancer and the hydrophilic polymer is alginate loaded with gemcitabine and the hydrophobic polymer is polycaprolactone loaded with paclitaxel.

In one embodiment, the amount of gemcitabine loaded into a solution of the hydrophilic alginate is in the range from about 1.2% to 1.5% by weight/volume.

In one embodiment, the rate of release of gemcitabine from the hydrophilic alginate solution is in the range from about 0.87 mg to about 1.3 mg in a first hour of measurement.

In one embodiment, the amount of paclitaxel loaded into a solution of the hydrophobic polycaprolactone is in the range from about 1.2% to 1.5% by weight/volume.

In one embodiment, the rate of release of paclitaxel from the hydrophobic polycaprolactone solution is in the range from about 0.25 mg to about 0.28 mg in a first hour of measurement.

In one embodiment, the coaxial fibre has a diameter in the wet state that falls within a range from about 1100 µm to about 1500 µm.

In one embodiment, the polymer core of the coaxial fibre has a diameter in a range from about 1000 µm to about 1200 µm and the polymer shell that surrounds the polymer core has a wall thickness that falls within a range from about 100 µm to about 300 µm.

In one embodiment, the polymer shell of the coaxial fibre has a pore size of about 0.1 µm to about 0.5 µm.

Preferably, the device further comprises a sheath encapsulating the coaxial fibre substantially therein.

In one embodiment, the sheath is formed from a polymer selected from the group consisting of polycaprolactone, poly(lactic acid), poly(lactic-co-glycolic acid), poly(propylene glycol) and a poly(l-amino acid).

In one embodiment, the sheath is modified to comprise a plurality of apertures disposed along the length of the sheath in spaced apart arrangement.

In one embodiment, each of the plurality of apertures has a diameter of about 100 µm.

Preferably, the device further comprises locating means for use in locating the implantable device when implanted into a subject.

In one embodiment, the locating means is configured for use in ultrasound detection and comprises a plurality of metal nanoparticles embedded substantially within at least one of the hydrophilic polymer and the hydrophobic polymer of the coaxial fibre.

In one embodiment, the metal nanoparticles are selected from the group consisting of: platinum, gold, silver, and any combination thereof.

In one embodiment, the locating means is configured for use in ultrasound detection and comprises a metal coating formed on an external surface of at least one of the hydrophilic polymer and the hydrophobic polymer of the coaxial fibre.

Preferably, the device further comprises a sheath encapsulating the coaxial fibre substantially therein, wherein the sheath comprises locating means in the form of a metal coating deposited on an external surface of the sheath.

In one embodiment, the metal coating comprises a metal selected from the group consisting of: platinum, gold, and any combination thereof.

According to a second aspect of the present invention there is provided a method of preparing an implantable device for use in treating a medical condition when implanted into a subject, the method comprising: preparing solutions of each of a hydrophilic polymer and a hydrophobic polymer, wherein at least one of said polymers is loaded with an agent that is active towards treating the medical condition; extruding the two solutions through a coaxial means; and collecting from the coaxial means, at least one coaxial fibre produced from the hydrophilic polymer and the hydrophobic polymer.

In one embodiment, wherein when the hydrophilic polymer corresponds to a core of the coaxial fibre and the hydrophobic polymer corresponds to a shell that surrounds the hydrophilic polymer core of the coaxial fibre, the extrusion occurs by: extruding the two solutions through the coaxial means into a coagulation bath comprising a coagulation agent.

According to a third aspect of the present invention there is provided a method of preparing an implantable device for use in treating a medical condition when implanted into a subject, the method comprising: preparing spinnable solutions of each of a hydrophilic polymer and a hydrophobic polymer, wherein at least one of said polymers is loaded with an agent that is active towards treating the medical condition; extruding the two spinnable solutions through a coaxial spinneret into a coagulation bath comprising a coagulation agent; and collecting from the coagulation bath, via a rotating mandrel, at least one coaxial fibre spun from the hydrophilic polymer and the hydrophobic polymer.

In one embodiment, the coagulation bath comprises a solution of ethanol and water.

In one embodiment, the coagulation agent is $CaCl_2$.

Preferably, the hydrophilic polymer corresponds to a core of the coaxial fibre and the hydrophobic polymer corresponds to a shell that surrounds the hydrophilic polymer core of the coaxial fibre.

In one embodiment, the hydrophobic polymer is polycaprolactone and the hydrophilic polymer is alginate.

In one embodiment, each of said hydrophilic polymer and said hydrophobic polymer is loaded with an agent that is active towards treating the medical condition.

Suitably, the active agent is a hydrophobic drug loaded into the hydrophobic polymer.

Suitably, the active agent is a hydrophilic drug loaded into the hydrophilic polymer.

Preferably, the method further comprises: coating the coaxial fibre with a polymer to form a sheath encapsulating the coaxial fibre substantially therein.

In one embodiment, the medical condition to be treated is cancer and the hydrophilic polymer is alginate loaded with gemcitabine and the hydrophobic polymer is polycaprolactone loaded with paclitaxel.

According to a third aspect of the present invention there is provided a method of delivering at least one active agent to a subject, the method comprising: implanting an implantable device according to the first aspect into a subject presenting with a medical condition that is treatable with the at least one active agent.

Preferably, the implanting is carried out using endoscopic ultrasound-guided implantation.

Other aspects of the invention are also disclosed.

BRIEF DESCRIPTION OF DRAWINGS

Notwithstanding any other forms which may fall within the scope of the present invention, preferred embodiments of the invention will now be described, by way of example only, with reference to the accompanying drawings in which.

DETAILED DESCRIPTION

It is to be understood that the following description is for the purpose of describing particular embodiments only and is not intended to be limiting with respect to the above description.

The present invention is predicated on the finding of an implantable drug delivery device that is designed to be implanted intratumourally, using a minimally invasive, clinically used implantation procedure called endoscopic ultrasound guided fine needle injection (EUS-FNI). Furthermore, and in contrast to many drug delivery studies to date, which focus on the delivery of a single therapeutic, the implantable device 10, 110 is configured to deliver more than one drug directly and simultaneously to a target site, thereby rendering it suitable for the treatment of such medical conditions as pancreatic ductal adenocarcinoma (PDAC), which responds to combinational chemotherapy.

Implantable Device

Figure 1:
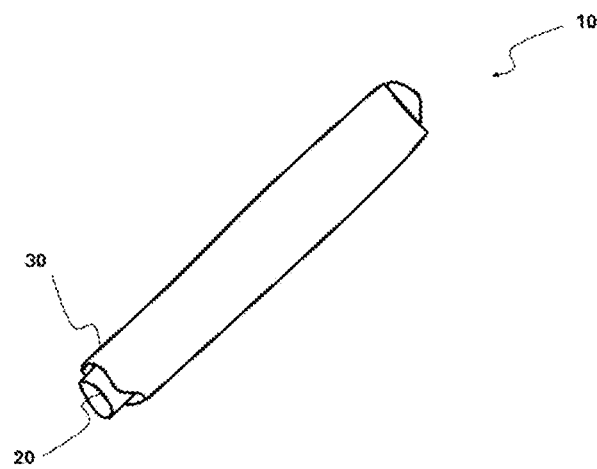
FIG. 1 shows a photograph of an implantable device for use in treating a medical condition when implanted into a subject according to a preferred embodiment of the present invention.

FIG. 1 shows a photograph of an implantable device 10 for use in treating a medical condition when implanted into a subject according to a preferred embodiment of the present invention.

Coaxial Fibre

Specifically, the implantable device 10 comprises a coaxial fibre 20 that is produced from polymers using a technique selected from the group consisting of wet spinning, electrospinning, coaxial melt extrusion printing, coaxial melt electro-writing, hot melt extrusion and pulsatile fibre spinning.

Using these techniques, the coaxial fibre 20 is typically produced by extruding the polymers through a coaxial means, which in the case of wet spinning is a spinneret, while in the case of coaxial melt extrusion printing, the coaxial means is a coaxial nozzle, and for hot melt extrusion, the coaxial means is a twin-screw extruder or two separate single screw extruders. In the case of hot melt extrusion, the molten polymer strands exiting the extruder(s) are then delivered to a spinneret for spinning into the coaxial fibre.

In a preferred embodiment, the coaxial fibre 20 is produced using a wet spinning technique using spinnable dope solutions of each of a hydrophilic polymer and a hydrophobic polymer.

The two polymer solutions each comprise an active agent suitable that is active towards treating the specific medical condition in question. The active agent present in the hydrophilic polymer solution is a hydrophilic drug, while the active agent present in the hydrophobic polymer is a hydrophobic drug.

The drug containing polymer solutions are then extruded together through a coaxial spinneret into a coagulation bath of an ethanol/water solution comprising a coagulation agent in the form of $CaCl_2$ to facilitate crosslinking and solidification. Once extruded, the resulting coaxial fibre 20 comprising the two drug loaded polymers is collected from the coagulation bath on a rotating mandrel and dried.

In one form, the coaxial fibre 20 is produced with the drug-loaded hydrophilic polymer being arranged at the core of the fibre 20 and the drug-loaded hydrophobic polymer surrounding the drug-loaded hydrophilic polymer core as a shell.

In an alternative form, the drug-loaded hydrophobic polymer is arranged at the core of the coaxial fibre 20 with the drug-loaded hydrophilic polymer surrounding the drug-loaded hydrophobic polymer core as a shell.

The hydrophobic polymer may be selected from the group consisting of polycaprolactone, poly(lactic acid), poly(lactic-co-glycolic acid), poly(2-oxazoline), polyglycerol sebacate, poly(propylene glycol) and a poly(l-amino acid). While the hydrophilic polymer may be selected from the group consisting of alginate, chitosan, carboxymethyl cellulose, poly(vinyl alcohol), hyaluronic acid and poly(ethylene glycol).

Active Agent

The active agent may be selected according to the specific medical condition in question. For instance, the active agent may be selected from the group consisting of: a chemotherapeutic agent (including but not limited to alkylating and alkylating-like agents, antimetabolites, antitumour antibiotics, plant alkaloids, hormones), a biologic (including but not limited to a monoclonal antibody, a tyrosine kinase inhibitor, RNAi, oligonucleotides, proteins, and aptamers, a peptide), an immune modulating agent (including but not limited to checkpoint inhibitor, tumour targeting monoclonal antibody (mAb) or fragment thereof, adoptive cell transfer, oncolytic viruses, DC-based interventions, immunostimulatory cytokines, immunomodulatory mAbs, inhibitors of immunosuppressive metabolism, PRR agonists, ICD inducers), a radioactive or radioisotope material, a contrast agent, a fluorescent dye, a steroid, a fatty acid, a vitamin, and any combination thereof.

For the purpose of demonstrating the effectiveness of the implantable device 10 in vivo, the following will describe its use in the treatment of pancreatic ductal adenocarcinoma (PDAC).

In this respect, the hydrophobic and hydrophilic drugs used to treat PDAC are chemotherapeutic agents.

For instance, the hydrophobic chemotherapeutic agent is selected from the group consisting of paclitaxel, camptothecan, everolimus, epothilone, curcumin, docetaxel, and any combination thereof. While the hydrophilic chemotherapeutic agent is selected from the group consisting of: gemcitabine, a platinum agent such as oxaliplatin, 5-fluorouracil, irinotecan, a taxane such as nab-paclitaxel, cyclophosphamide, rituximab, cetuximab, trastuzumab, pertuzumab, sunitinib, bevacizumab, an anti-EGFR molecule such as erlotinib, an anti-CTLA4 antibody such as ipilimumab, an anti-PD1 or anti-PDL1 antibody or inhibitor such as pembrolizumab or nivolumab, tisagenlecleucel, an immune modulating agent such as talimogene laherparepvec, and any combination thereof.

Good results have been obtained when the hydrophilic polymer at the core of the coaxial fibre 20 is alginate loaded with gemcitabine and the hydrophobic polymer shell surrounding the gemcitabine-loaded alginate core is polycaprolactone loaded with paclitaxel. Polycaprolactone rapidly coagulates and solidifies during the wet spinning process, thereby protecting the alginate core from exposure to the coagulation bath, and subsequent loss of gemcitabine.

Ideally, the coaxial fibre 20 is produced by spinning a polymer dope comprising from about 15% to 20% polycaprolactone by weight/volume in solution and about 3% to 5% alginate by weight/volume. That is, the coaxial fibre 20 is produced by spinning a polymer dope comprising from about 0.05% to about 0.1% polycaprolactone by weight, and about 0.9% to about 0.95% alginate by weight relative to the polycaprolactone.

It will be appreciated that when the coaxial fibre 20 is placed in a physiological solution swelling occurs. The inventors have found that the coaxial fibre 20 typically swells to a diameter in the wet state that falls within a range from about 1100 μm to 1500 μm.

In this respect, the gemcitabine-loaded alginate core of the coaxial fibre 20 has a diameter that falls within a range from about 1000 µm to about 1200 µm and the paclitaxel-loaded polycaprolactone shell that surrounds the gemcitabine-loaded alginate core has a wall thickness that falls within a range from about 100 µm to about 300 µm, and an overall pore size of about 0.1 µm to 0.5 µm.

Table 1 provides a comparison of diameters (µm) of a set of coaxial fibres 20 in the wet state (measured under vacuum) prepared according to the wet spinning process, in which the coaxial fibre 20 comprises (A) paclitaxel and gemcitabine, (B) no paclitaxel and gemcitabine, (C) just gemcitabine, and (D) just paclitaxel.

TABLE 1

|  | A | B | C | D |
|---|---|---|---|---|
| Diameter (µm) | 1466.4 | 1408.8 | 1416.9 | 1273.4 |
|  | 1488.1 | 1369.6 | 1406.7 | 1232.7 |
|  | 1512.6 | 1352.1 | 1389 | 1186.6 |
|  | 1401.8 | 1388.9 | 1393.1 | 1038.6 |
|  | 1338.1 | 1401.3 | 1358.6 | 1051.3 |
|  | 1367.5 | 1402.8 | 1332.2 | 1132.5 |
|  | 1197.6 | 1423.7 |  | 1386.9 |
|  | 1182.7 | 1437.6 |  | 1405.4 |
|  | 1178.9 | 1437.6 |  | 1394 |
|  | 1163.2 | 1295.6 |  | 1438.1 |
|  | 1094.4 | 1278.9 |  | 1383.6 |
|  | 1110 | 1289.4 |  | 1408.2 |
| Average Diameter (µm) | 1291.8 | 1373.9 | 1382.8 | 1277.6 |

As found, the average diameters of the coaxial fibres 20 vary little with drug loading.

Drug Loading

The theoretical drug loading of gemcitabine and/or paclitaxel was calculated using the known concentration (µg/mL) of the drug in the polymer solution, the spinning rate (mL/min) of the solution and the rate at which the fibre forms (m/min).

Using these values and equation (1) it is possible to determine the encapsulation efficiency using equation (2)

$$\text{Theoretical Loading} = \frac{C \times SR}{FF} = \mu g/m \quad (1)$$

Where C is the concentration, SR is the spinning rate, and FF is fibre formation rate $$\text{Encapsulation Efficiency} = \frac{\text{Actual Loading}}{\text{Theoretical Loading}} \times 100 \quad (2)$$

The amount of gemcitabine loaded into the hydrophilic alginate was calculated to be in the range from about 1.2% to 1.5% by weight. While the amount of paclitaxel loaded into the hydrophobic polycaprolactone was calculated to also be in the range from about 1.2% to 1.5% by weight.

Figure 2:
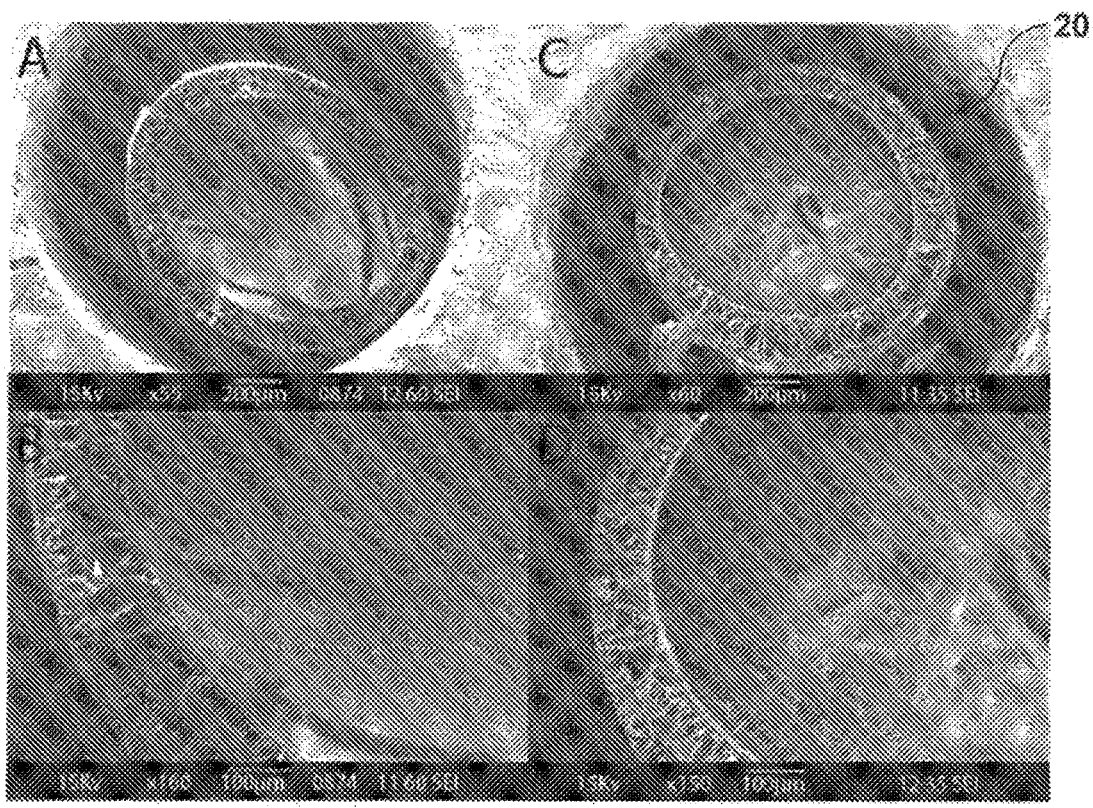
FIG. 2 shows scanning electron microscopy (SEM) images of cross sections of a coaxial fibre of the implantable device of FIG. 1, before (A, B) and after (C, D) loading a hydrophilic core and hydrophobic shell of the coaxial fibre with gemcitabine and paclitaxel, respectively, (A, C—Scale: 200 μm, B, D—Scale 100 μm)

FIG. 2 shows scanning electron microscopy (SEM) images of the internal morphology of cross sections of a coaxial fibre 20 taken before (A, B) and after (C, D) loading a hydrophilic core and hydrophobic shell of the coaxial fibre 20 with gemcitabine and paclitaxel, respectively. Here, it was observed that the addition of the hydrophobic and hydrophilic drugs to the respective polymers did not adversely affect the internal structure of the coaxial fibre 20.

Sheath

In a preferred form, the implantable device 10 further comprises a sheath 30 for use in encapsulating the coaxial fibre 20 substantially therein, as a means by which to protect the coaxial fibre 20 during the implantation method, and to control the release of the drugs loaded therein.

The sheath 30 is ideally formed from a polymer selected from the group consisting of polycaprolactone, poly(lactic acid), poly(lactic-co-glycolic acid), poly(propylene glycol) and a poly(l-amino acid).

In a preferred form, the sheath 30 is polycaprolactone.

Figure 3:
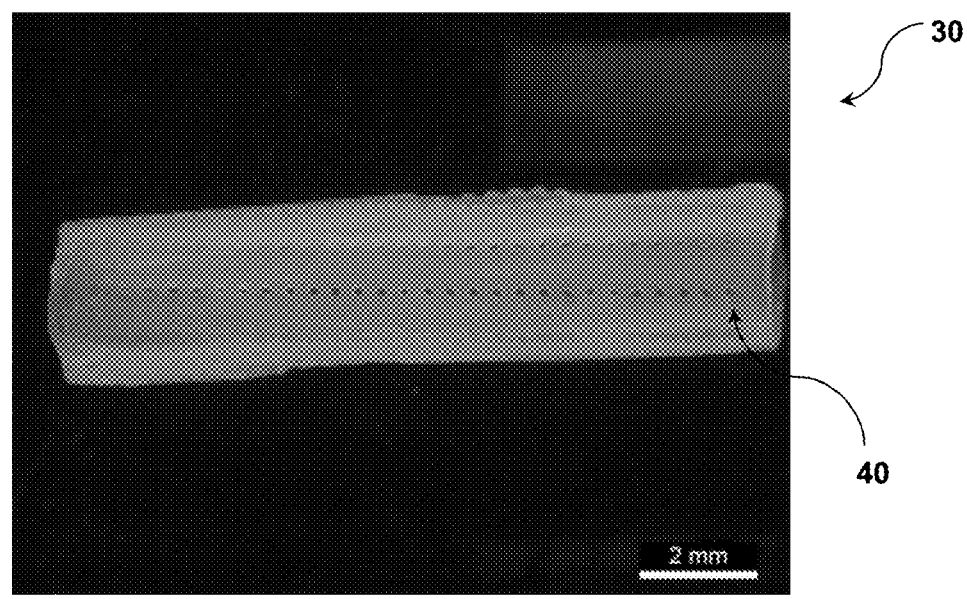
FIG. 3 shows a photograph of a sheath of the implantable device of FIG. 1 for use in encapsulating a coaxial fibre of the implantable device, (Scale: 2 mm)

FIG. 3 shows a photograph of the polycaprolactone sheath 30 for use in encapsulating the coaxial fibre 20 of the implantable device 10.

As shown, the sheath 30 has been modified using laser cutting to comprise a plurality of apertures 40 disposed along the length of the sheath 30 in spaced apart arrangement for use in providing mechanical strength without impeding the release of the drugs loaded within the coaxial fibre 20.

Good results have been obtained when each of the apertures 40 has a diameter of about 100 µm.

Figure 4:
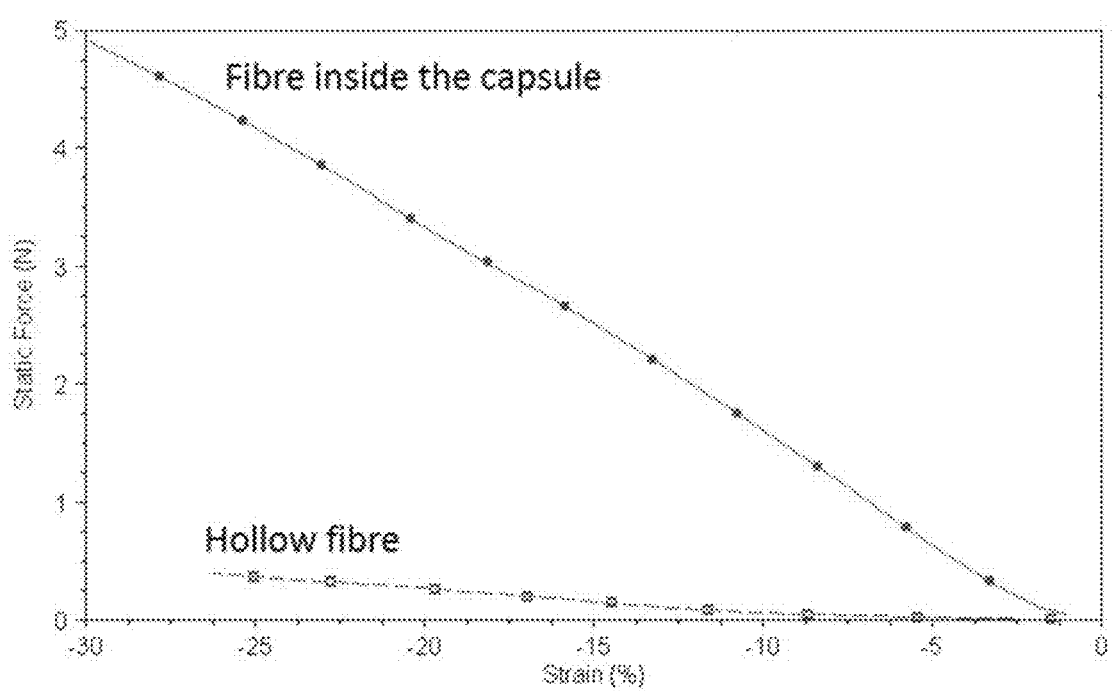
FIG. 4 shows a plot (Static Force (N) versus Strain (%)) that compares the mechanical properties of the coaxial fibre with that of a polycaprolactone sheathed coaxial fibre.

FIG. 4 shows a plot (Static Force (N) versus Strain (%)) that compares the mechanical properties of the coaxial fibre 20 with that of the polycaprolactone sheathed coaxial fibre 20. These results indicate that there is a substantial improvement in the mechanical properties of the coaxial fibre 20 by placing it within the sheath 30. Such improvements in the mechanical properties are necessary to enable implantation in tissue or tumour.

Echogenicity

To aid in the placing and tracking of the implantable device 10 in a subject in vivo, the implantable device 10 further comprises locating means.

The inventors have determined that the echogenicity of the implant is crucial for correct placement and is something that has been little considered in the field of implantable drug delivery systems.

In one embodiment, the locating means is configured for use in ultrasound detection and comprises a plurality of metal nanoparticles embedded substantially within at least one of the hydrophilic polymer and the hydrophobic polymer of the coaxial fibre 20. The metal nanoparticles may be selected from the group consisting of: platinum, gold, silver, and any combination thereof.

In the case of a coaxial fibre 20 having a gemcitabine-loaded alginate core and a paclitaxel-loaded polycaprolactone shell, good results have been obtained when the alginate core is loaded with gold nanoparticles (AuNP), to produce an implantable device 10 that is echogenic, and thus detectable in vivo using ultrasound imaging.

In an alternative embodiment, the locating means may take the form of a metal coating (for example, a gold, platinum, or platinum/gold alloy coating) formed on an external surface of at least one of the hydrophilic polymer and the hydrophobic polymer of the coaxial fibre 20, or on an external surface of the sheath 30.

Implantation Method

According to another preferred embodiment of the present invention there is provided a method of delivering one or more active agents to a subject in vivo using the implantable device 10 described above.

The method comprises as a first step, the step of implanting the implantable device 10 into a subject presenting with a medical condition that is treatable with the active agent.

In the described example, the medical condition to be treated is pancreatic ductal adenocarcinoma (PDAC), and thus the implantable device 10 has a coaxial fibre 20 that is prepared from a gemcitabine-loaded alginate core further loaded with AuNP, and a paclitaxel-loaded polycaprolactone shell—namely, chemotherapeutic agents.

As indicated above, the procedure used to implant the device 10 into a PDAC tumour is called endoscopic ultrasound-guided fine needle injection (EUS-FNI). A description detailing the use of EUS-FNI for use in implanting within solid pancreatic tumours is provided in the literature,[3] which is incorporated herein by reference.

Results

Drug Release

Figure 5:
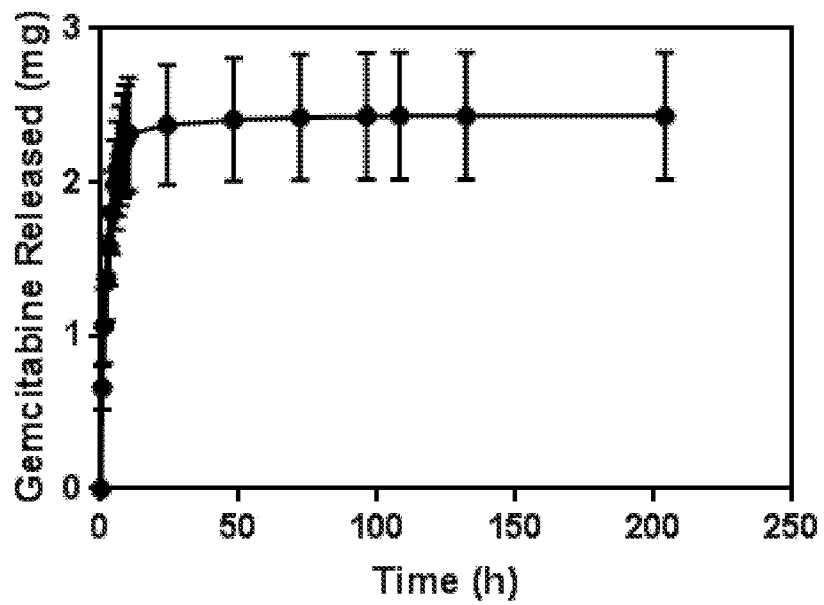
FIG. 5 shows a plot that reveals the amount (mg) of gemcitabine that is released from the hydrophilic core of the coaxial fibre performed at 37° C. over a 7-day period (measurement repeated three times to obtain an average reading)

FIG. 5 shows a plot that reveals the amount (mg) of gemcitabine that is released from the gemcitabine-loaded alginate core of the coaxial fibre 20 when performed at 37° C. over a 7-day period (measurement repeated three times to obtain an average reading). Here, the rate of release of gemcitabine from the hydrophilic gemcitabine-loaded alginate core is in the range from about 0.87 mg to 1.3 mg in the first hour of measurement.

Figure 6:
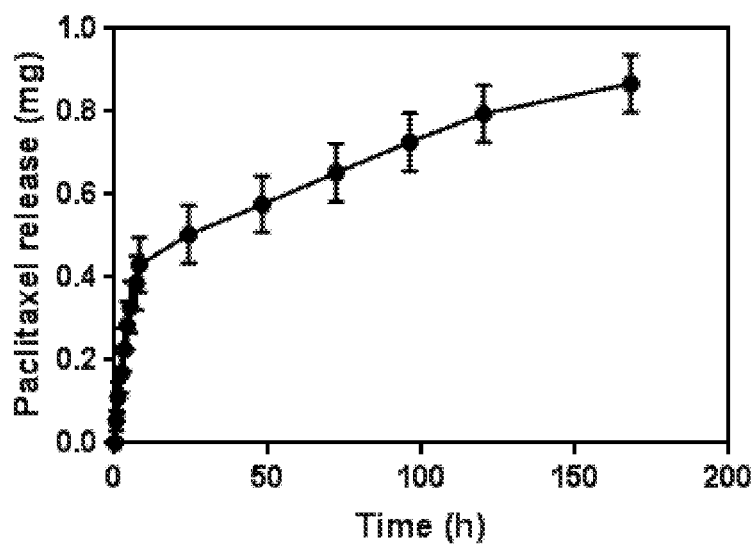
FIG. 6 shows a plot that reveals the amount (mg) of paclitaxel that is released from the hydrophobic shell of the coaxial fibre performed at 37° C. over a 7-day period (measurement repeated three times to obtain an average reading)

FIG. 6 shows a plot that reveals the amount (mg) of paclitaxel that is released from the paclitaxel-loaded polycaprolactone shell of the coaxial fibre 20, when performed at 37° C. over a 7-day period (measurement repeated three times to obtain an average reading). Here, the rate of release of paclitaxel from the hydrophobic paclitaxel-loaded polycaprolactone shell is in the range from about 0.25 mg to 0.28 mg in the first hour of measurement.

Cell Viability

PANC-1 and MIA-PaCa-2 human PDAC pancreatic cancer cells were grown as a monolayer and treated with 0.5 cm long coaxial fibres 20 with varying drug loadings over a 24 h, 48 h, and 72 h period.

Figure 7:
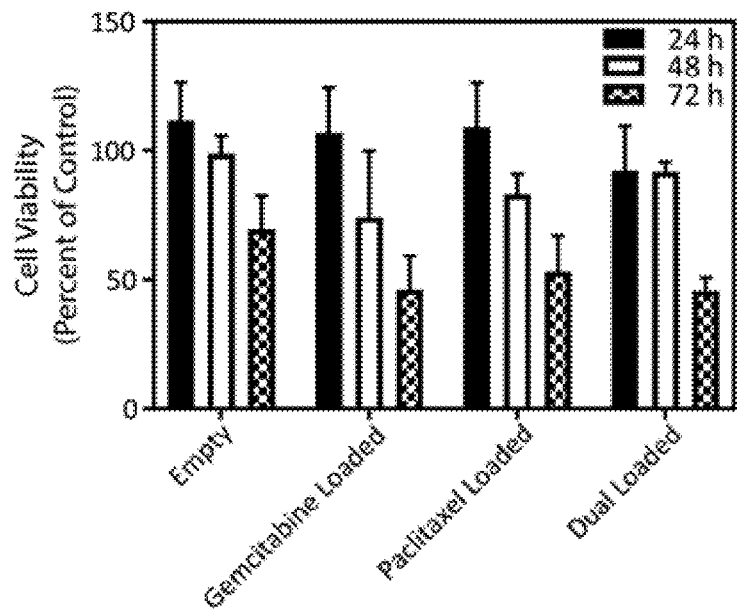
FIG. 7 shows a plot that reveals the cell viability (% of untreated control) of the MIA PaCa-2 pancreatic cancer cell line after treatment with (i) a coaxial fibre without any preloaded drugs, and (ii) a coaxial fibre loaded with (a) gemcitabine, (b) paclitaxel and (c) both gemcitabine and paclitaxel, when measured at 37° C. over a 24 h, 48 h, and 72 hour period.

Specifically, FIG. 7 shows a plot that reveals cell viability (% of untreated control) of the MIA PaCa-2 pancreatic cancer cell line after treatment with (i) a coaxial fibre 20 prepared without any preloaded drugs, and (ii) a coaxial fibre 20 loaded with either (a) gemcitabine, (b) paclitaxel or (c) both gemcitabine and paclitaxel, when measured at 37° C. over this 24 h, 48 h, and 72 h hour period.

Here, the inventors observed that the MIA-PaCa-2 cells treated with the coaxial fibres 20 loaded with both gemcitabine and paclitaxel showed a slight reduction in cell viability when compared to the coaxial fibres 20 loaded with either gemcitabine or paclitaxel at 48 h (45.8% vs 46.2% and 53.2%, respectively).

Figure 8:
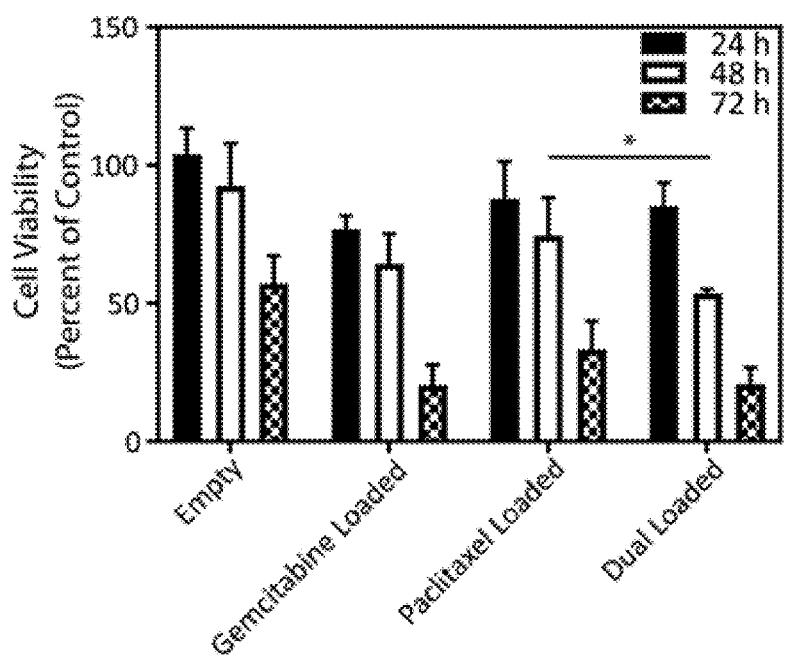
FIG. 8 shows a plot that reveals the cell viability (% of untreated control) of the PANC-1 pancreatic cancer cell line after treatment with (i) a coaxial fibre without any preloaded drugs, and (ii) a coaxial fibre loaded with (a) gemcitabine, (b) paclitaxel and (c) both gemcitabine and paclitaxel, when measured at 37° C. over a 24 h, 48 h, and 72 hour treatment period.

FIG. 8 shows a plot that reveals cell viability (% of untreated control) of the PANC-1 pancreatic cancer cell line after treatment with (i) a coaxial fibre 20 prepared without any preloaded drugs, and (ii) a coaxial fibre 20 loaded with either (a) gemcitabine, (b) paclitaxel or (c) both gemcitabine and paclitaxel, when measured at 37° C. over this 24 h, 48 h, and 72 h hour period.

Here, the inventors observed that the PANC-1 cells treated with the coaxial fibres 20 loaded with both gemcitabine and paclitaxel showed a greater reduction in cell viability than the coaxial fibres 20 loaded with either gemcitabine or paclitaxel at 48 h (41.4% vs 48.6% and 60.5% respectively).

At 72 h, the coaxial fibres 20 loaded with both gemcitabine and paclitaxel showed an equivalent reduction in cell viability to that of the coaxial fibres 20 loaded with gemcitabine, but still greater reductions than the coaxial fibres 20 loaded with paclitaxel (20.8% vs 20.5% and 33.3% respectively). A time dependent decrease in viability was observed in all treatment groups.

Growth Inhibition of 3D Tumour Spheroids

In order to further quantify the efficacy of these coaxial fibre 20 formulations, an established 3D tumour spheroid model was utilised. Tumour spheroids are an intermediate between the over simplified 2D monolayer model, which is a high throughput method for assessing initial toxicity, and animal models. Spheroids contain complexities present in in vivo tumours, such as active nutrient, metabolism, and oxygen cycles when reaching a size of 200-500 μm. They develop a proliferative outer layer and a necrotic core at this size, which is a common feature of many solid tumours. KPC mouse PDAC cell line was chosen as the spheroid model instead of PANC-1, as PANC-1 form looser, less compact spheroids when grown in media (compared to KPC), which less accurately represents the dense fibrotic nature of the disease.

KPC spheroids were treated with 0.5 cm long coaxial fibres 20 with varying drug loadings over a 5-day period.

Figure 9:
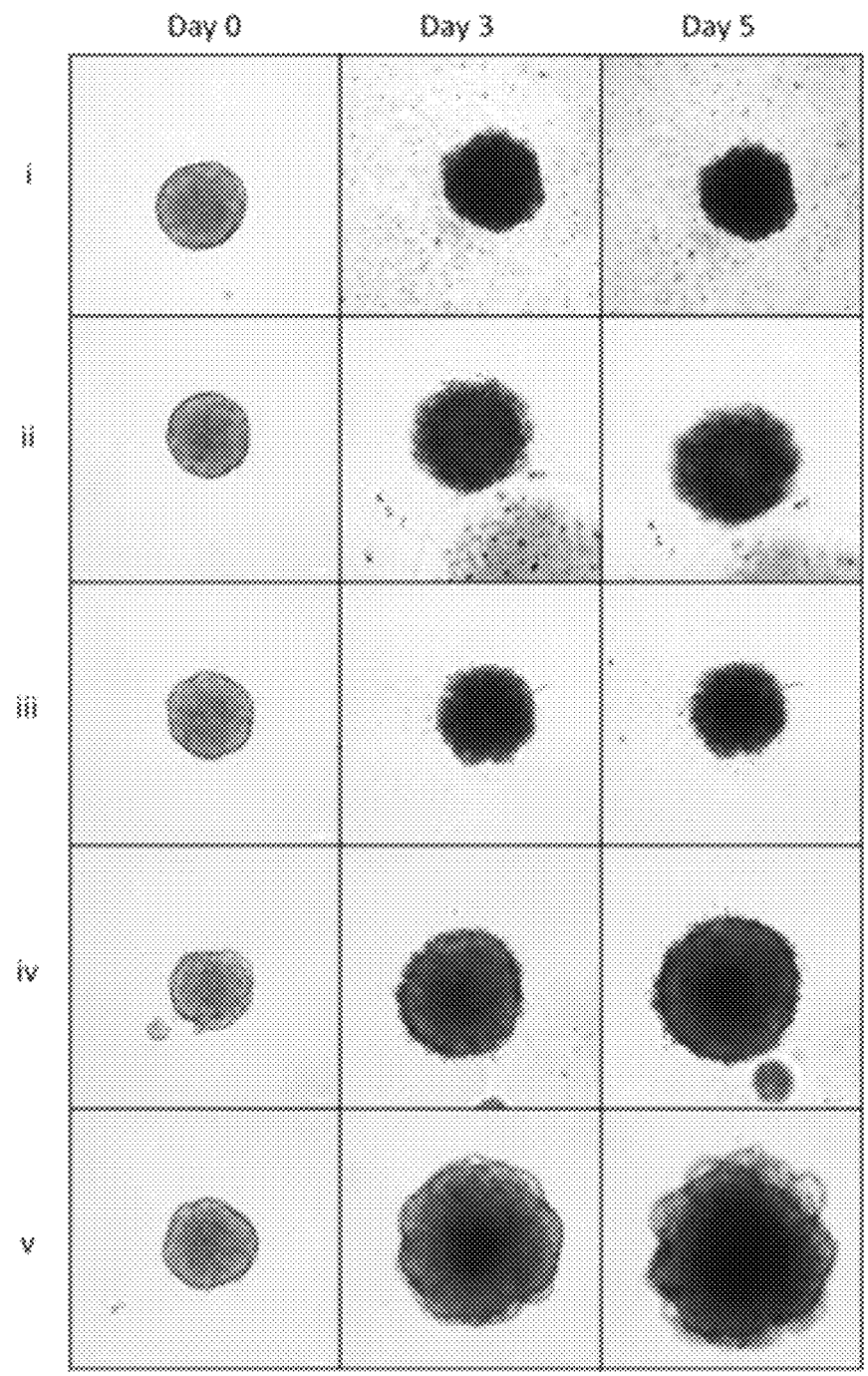
FIG. 9 shows light microscopy images (10× magnification) of KPC spheroids after treatment with (i) a coaxial fibre loaded with gemcitabine, (ii) a coaxial fibre loaded with paclitaxel, (iii) a coaxial fibre loaded with both gemcitabine and paclitaxel, (iv) a coaxial fibre without any preloaded drugs, and (v) a control, when measured at 37° C. over a 5 day treatment period.

Specifically, FIG. 9 shows light microscopy images (10× magnification) of these KPC spheroids after treatment with (i) a coaxial fibre 20 loaded with gemcitabine, (ii) a coaxial fibre 20 loaded with paclitaxel, (iii) a coaxial fibre 20 loaded with both gemcitabine and paclitaxel, (iv) a coaxial fibre 20 without any preloaded drugs, and (v) a control, when measured at 37° C. over this 5 day period.

As shown in FIG. 9 (i)-(iii), the corresponding microscopy images reveal that the coaxial fibres 20 loaded with gemcitabine, paclitaxel, and both gemcitabine and paclitaxel, have a cytotoxic effect on the cells, as can be seen by the lack of growth and the lack of a visible necrotic core.

The development of the necrotic core can be visualised in the spheroids treated with coaxial fibres 20 devoid of gemcitabine and paclitaxel (FIG. 9 (iv)) and in the untreated cells provided as a control (FIG. 9(v)), which is indicative of spheroid proliferation.

Figure 10:
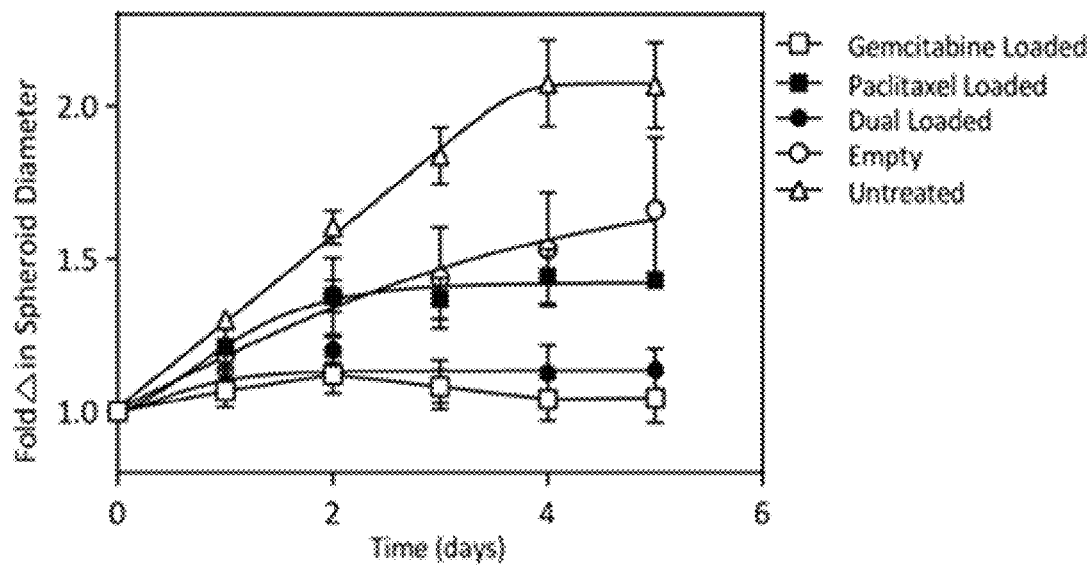
FIG. 10 shows a plot that reveals the fold change in diameter of KPC spheroids after treatment with (i) a coaxial fibre loaded with gemcitabine, (ii) a coaxial fibre loaded with paclitaxel, (iii) a coaxial fibre loaded with both gemcitabine and paclitaxel, (iv) a coaxial fibre without any preloaded drugs, and (v) a control, when measured at 37° C. over the same 5 day treatment period (as determined from bright-field images acquired at 10× magnification)

FIG. 10 shows a plot that reveals the fold change in diameter of the KPC spheroids after treatment with (i) a coaxial fibre 20 loaded with gemcitabine, (ii) a coaxial fibre 20 loaded with paclitaxel, (iii) a coaxial fibre 20 loaded with both gemcitabine and paclitaxel, (iv) a coaxial fibre 20 without any preloaded drugs, and (v) untreated cells as a control, when measured at 37° C. over the same 5 day period (as determined from bright-field images acquired at 10× magnification).

Here, the inventors observed that the diameter of the KPC spheroids (measured daily) showed an initial increase in diameter for all treatments, but then by day five, there was a notable reduction or slowing in the change in diameter for those cells treated with coaxial fibres 20 loaded with gemcitabine, paclitaxel, and both gemcitabine and paclitaxel (1.04, 1.43 and 1.14 fold increase, respectively).

While in the case of the cells treated with coaxial fibres 20 devoid of any drugs, and the untreated cells, there was an observed increase in diameter (1.66 and 2.07-fold increase, respectively).

Figure 11:
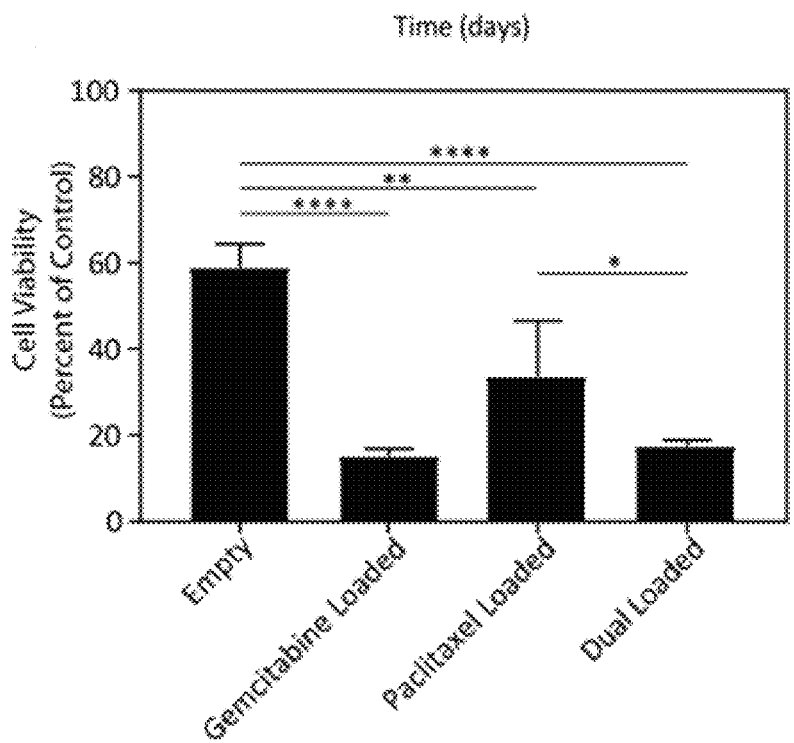
FIG. 11 shows a plot that reveals the cell viability (% of untreated control) of KPC spheroids treated with (i) a coaxial fibre without any preloaded drugs, (ii) a coaxial fibre loaded with gemcitabine, (iii) a coaxial fibre loaded with paclitaxel, and (iv) a coaxial fibre loaded with both gemcitabine and paclitaxel, at the conclusion of the same 5 day treatment period (data points are the mean of quintuplicate values±SD. *P=0.05, P≤0.01, **P=0.0001)

FIG. 11 shows an endpoint APH assay that reveals that the cell viability (% of untreated control) of the KPC spheroids treated with (i) a coaxial fibre 20 without any preloaded drugs, (ii) a coaxial fibre 20 loaded with gemcitabine, (iii) a coaxial fibre 20 loaded with paclitaxel, and (iv) a coaxial fibre 20 loaded with both gemcitabine and paclitaxel, at the conclusion of the 5 day treatment period (data points are the mean of quintuplicate values±SD. *P=0.05, P≤0.01, **P=0.0001).

Here, the inventors observed that the cells treated with coaxial fibres 20 loaded with gemcitabine, paclitaxel, and both gemcitabine and paclitaxel retain 15.0, 33.7 and 17.5% cell viability, respectively.

Although the viability of the spheroids treated with coaxial fibres 20 devoid of any drugs is reduced after 5 days, the images show that the spheroids a tight diameter and a consistent growth rate over the 5 days.

Figure 12:
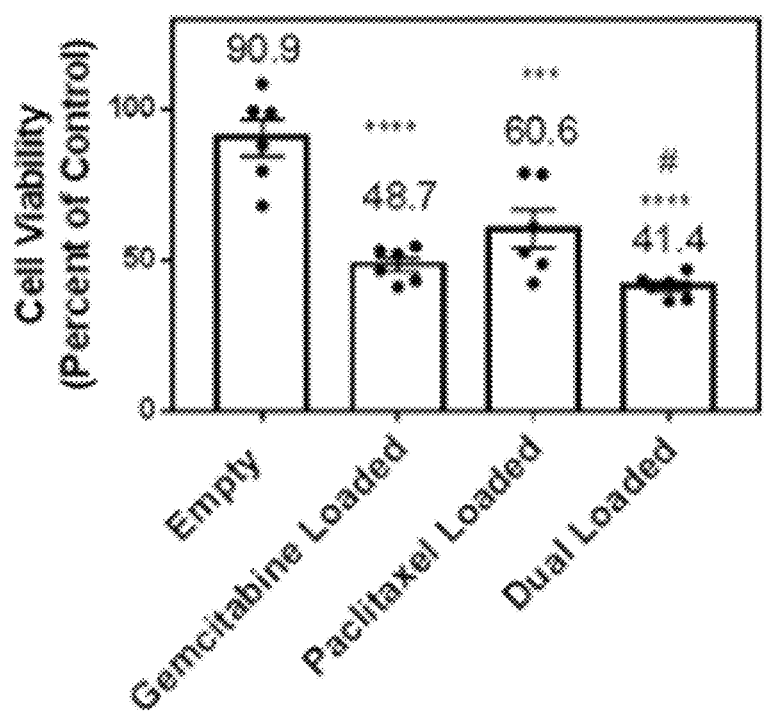
FIG. 12 shows a plot that reveals the cell viability (% of untreated control) of KPC spheroids treated with (i) a coaxial fibre without any preloaded drugs, (ii) a coaxial fibre loaded with gemcitabine, (iii) a coaxial fibre loaded with paclitaxel, and (iv) a coaxial fibre loaded with both gemcitabine and paclitaxel, at the conclusion of the same 5 day treatment period. Data points are the mean of quintuplicate values±SD. *P=0.05, P≤0.01, **P=0.0001.

FIG. 12 shows a plot that reveals the cell viability (% of untreated control) of KPC spheroids treated with (i) a coaxial fibre 20 without any preloaded drugs, (ii) a coaxial fibre loaded with gemcitabine, (iii) a coaxial fibre 20 loaded with paclitaxel, and (iv) a coaxial fibre 20 loaded with both gemcitabine and paclitaxel, at the conclusion of the same 5 day treatment period.

The results from FIG. 12 show that the KPC spheroids treated with a coaxial fibre 20 loaded with both gemcitabine and paclitaxel have a reduced cell viability (%) when compared to spheroids treated with either the single drug-loaded coaxial fibre 20, the empty coaxial fibre 20, or simply when left untreated.

Organotypic Assay

Figure 13:
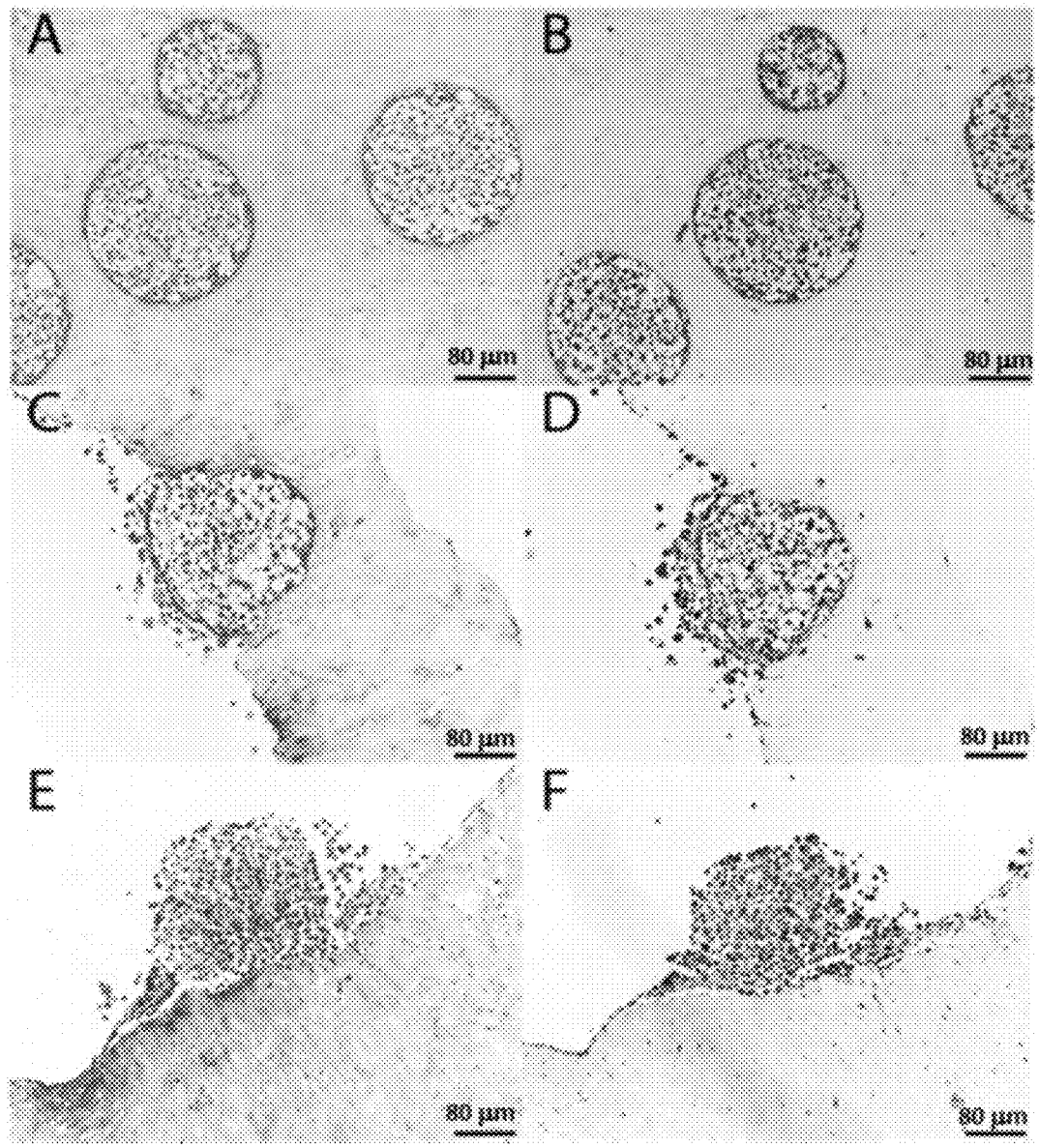
FIG. 13 shows photomicrographs (10× magnification) of organotypic matrices stained with picrosirius red (left column) and H&E (right column), treated with (A, B) a coaxial fibre loaded with gemcitabine and paclitaxel, (C, D) a coaxial fibre without any preloaded drugs, and (E, F) an untreated control, (Scale: 80 μm)

FIG. 13 shows photomicrographs (10× magnification) of organotypic matrices stained with picrosirius red (left column) and H&E (Haematoxylin and Eosin (right column), treated with (A, B) a coaxial fibre 20 loaded with gemcitabine and paclitaxel, (C, D) a coaxial fibre 20 without any preloaded drugs, and (E, F) an untreated control.

Here, the collagen matrices that were treated with a coaxial fibre 20 without any preloaded drugs or were left untreated showed similar results to one another, in which the tumour spheroid migrated out of the collagen. The matrices treated with the coaxial fibre 20 loaded with gemcitabine and paclitaxel however, had tumour spheroids that remained embedded within the matrix, exhibiting reduced migration and progression.

Figure 14:
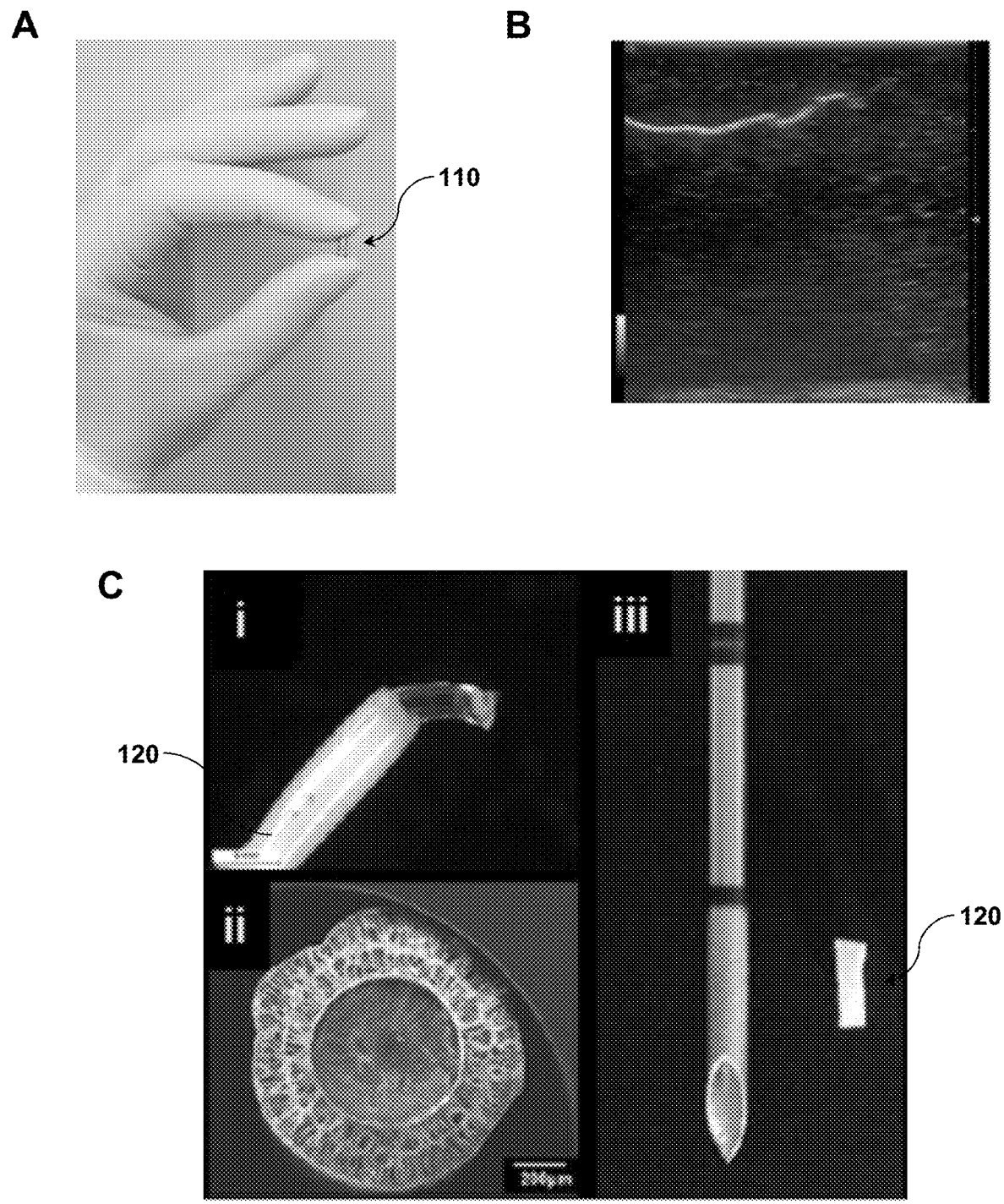
FIG. 14 shows A) a photograph of a PCL-Alg coaxial fibre implantable device for use in treating a medical condition when implanted into a subject according to another preferred embodiment of the present invention, B) an ultrasound image showing that the PCL-Alg coaxial fibre of the implantable device is visible under ultrasound, C) shows (i) a side view of the PCL-Alg coaxial fibre (core exposed) in the hydrated state, (ii) a cross-sectional scanning electron microscopy image of the PCL-Alg core-shell morphology of the coaxial fibre (scale: 200 μm); (iii) and a photograph of the PCL-Alg coaxial fibre of the implantable device (of length 1 cm) in the dehydrated state, positioned side by side with an endoscope needle (19 gauge) for reference.

FIG. 14 shows various images showing the internal and external core-shell morphology and size of a coaxial fibre implantable device 110 (of length 1 cm) for use in treating a medical condition when implanted into a subject according to another embodiment of the present invention.

As shown in FIG. 14, the implantable device 110 comprises a coaxial fibre 120 that is again formed using a technique selected from the group consisting of wet spinning, electrospinning, coaxial melt extrusion printing, coaxial melt electro-writing, hot melt extrusion and pulsatile fibre spinning.

In a preferred embodiment, the coaxial fibre 120 is produced using a wet spinning technique using spinnable solutions of each of a hydrophilic polymer in the form of alginate (Alg) and a hydrophobic polymer in the form of polycaprolactone (PCL).

In a preferred embodiment, the concentration of alginate (Alg) is about 3% and the concentration of PCL is about 15%.

In one embodiment, the coaxial fibre implantable device 110 may also be sheathed by a polycaprolactone (PCL) sheath (not shown).

Figure 15:
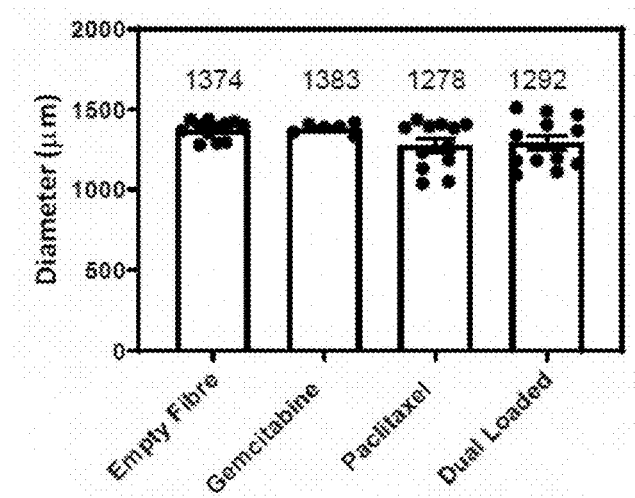
FIG. 15 shows a plot that reveals the diameter (μm) of coaxial fibres produced using a wet spinning technique (measured after drying) with a coaxial fibre without any preloaded drugs ("Empty Fibre"), a coaxial fibre loaded with gemcitabine ("Gemcitabine"), a coaxial fibre loaded with paclitaxel ("Paclitaxel"), and a coaxial fibre loaded with both gemcitabine and paclitaxel ("Dual Loaded"). The bars represent the mean of n=12 measurements±SEM.

FIG. 15 shows a plot that reveals that the diameter (μm) of the coaxial fibres 120 is not impacted by the addition of the drugs, gemcitabine and/or paclitaxel.

Figure 16:
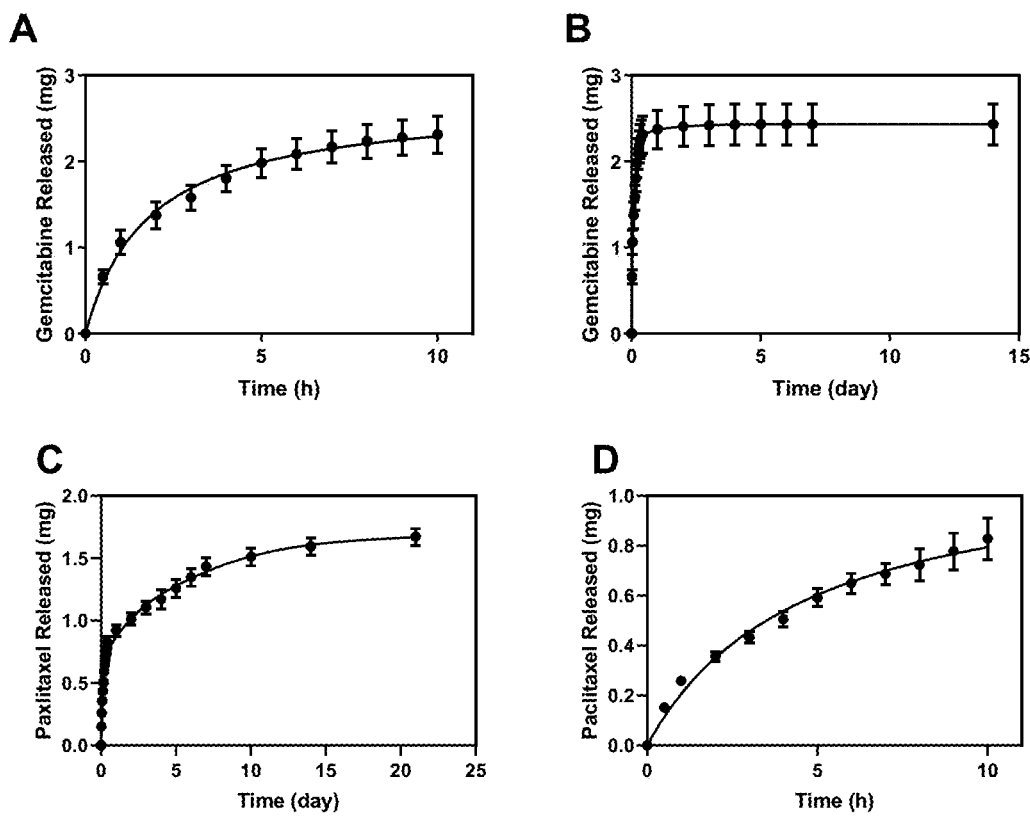
FIG. 16 shows plots that reveal the amount (mg) of (A, B) gemcitabine and (C, D) paclitaxel that is released from the hydrophobic shell of the coaxial fibre performed at 37° C. over a 14-21-day period (measurement repeated three times to obtain an average reading)

FIG. 16 shows a series of four plots that reveal the amount (mg) of (A, B) gemcitabine and (C, D) paclitaxel that is released from the hydrophobic PCL shell of the coaxial fibre 120 performed at 37° C. over a 14-21-day period.

As shown in plots A) and B), gemcitabine displays a rapid drug release from the hydrophobic PCL shell of the coaxial fibre 120, while in plots C) and D), paclitaxel displays a much slower, more sustained release from the hydrophobic PCL fibre over time.

Figure 17:
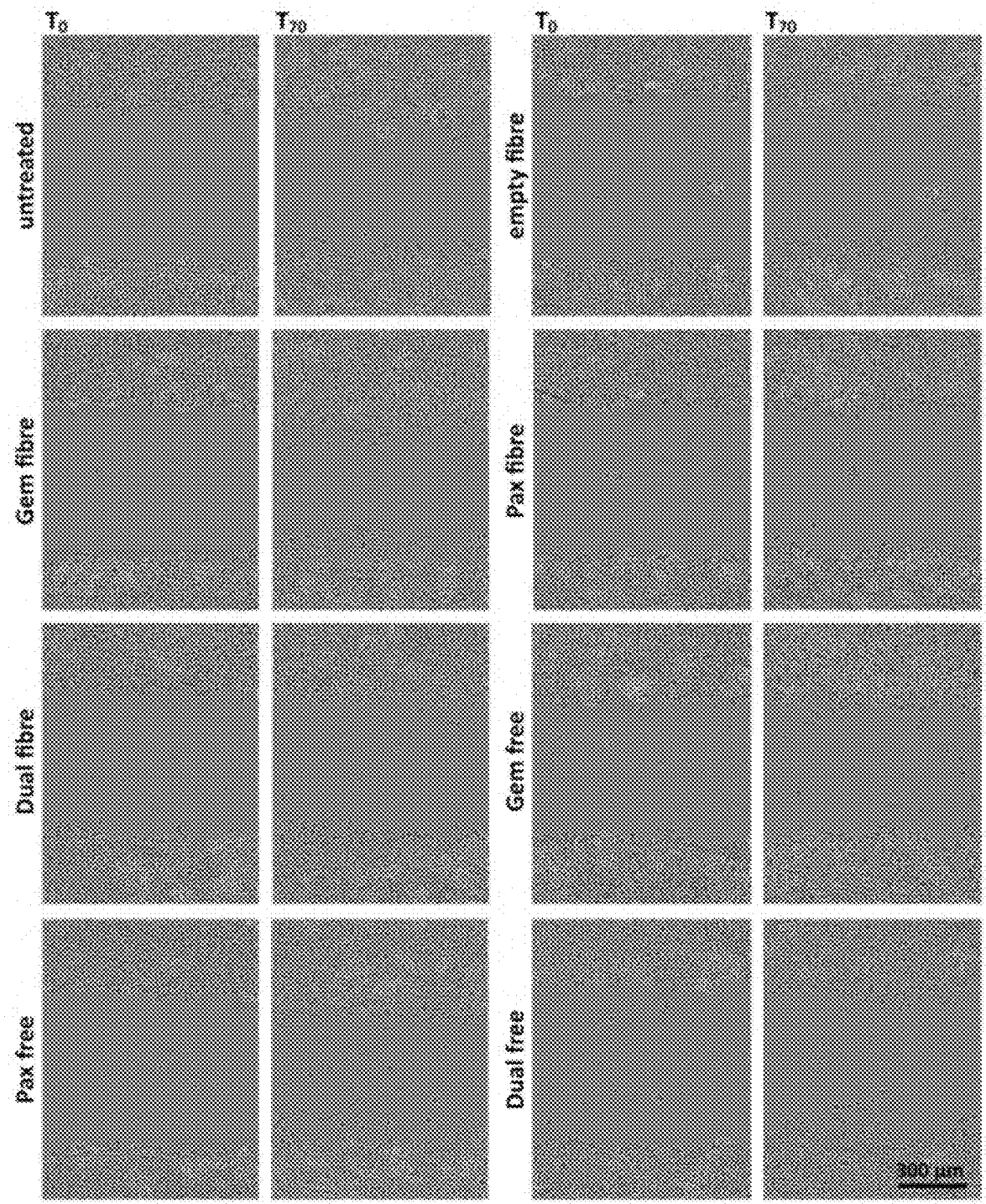
FIG. 17 shows a scratch migration assay that reveals the progression of cell migration of MIA-PaCa-2 cells at $T_0$ and $T_{70}$ for a coaxial fibre without any preloaded drugs ("empty fibre"), a coaxial fibre loaded with gemcitabine ("Gem fibre"), a coaxial fibre loaded with paclitaxel ("Pax fibre"), and a coaxial fibre loaded with both gemcitabine and paclitaxel ("Dual fibre"), when compared to a series of controls including: untreated MIA-PACa-2 cell control ("untreated"), free gemcitabine ("Gem free"), free paclitaxel ("Pax free"), and a combination of free gemcitabine and free paclitaxel ("Dual free"), (Scale: 300 μm)

FIG. 17 shows an in vitro scratch migration assay conducted on a cell monolayer to mimic the effect of cell migration that occurs during wound healing and cancer cell migration in vivo. This study of the migration of MIA-PaCa-2 pancreatic cancer cells (taken at $T_0$ and $T_{70}$), together with the wound width reduction data provided in the plots shown in FIGS. 18 and 19, clearly shows that when the drugs (gemcitabine and/or paclitaxel) are eluted from a coaxial fibre 120 preloaded with said one or both drugs, there is no significant difference during cell migration when compared to the corresponding data associated with the free drugs themselves, thereby indicating bioequivalence.

Figure 20:
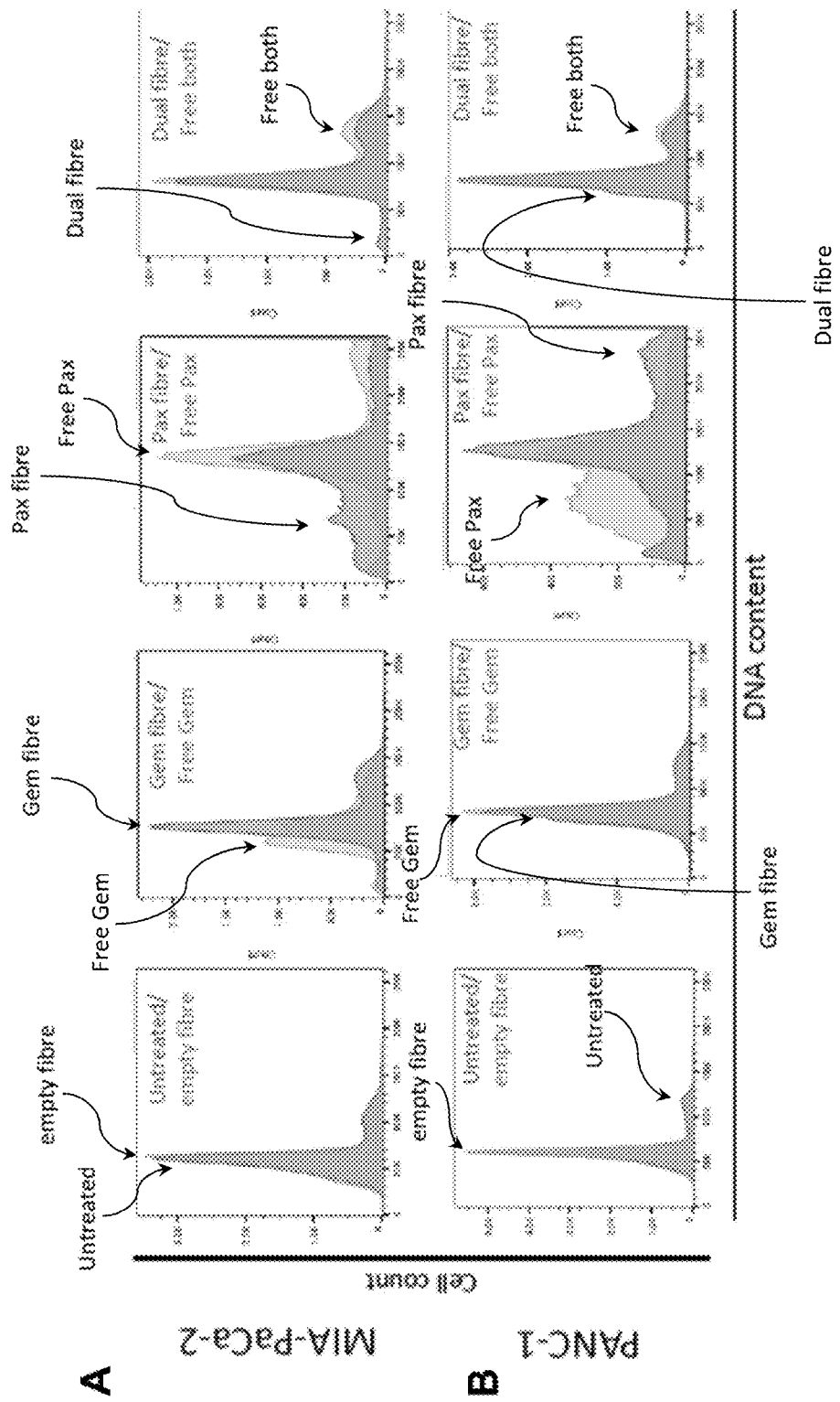
FIG. 20 shows a flow-cytometric cell cycle analysis using Vybrant™ DyeCycle™ Violet Stain DNA staining of A) MIA-PaCa-2 cells and B) PANC-1 cells, which reveals gemcitabine ("Gem fibre/Free Gem"), paclitaxel ("Pax fibre/Free Pax"), or a combination of and paclitaxel ("Dual fibre/Free both") eluted from a coaxial fibre preloaded with said drug/drug combination, induces cell cycle changes similar to the free drugs themselves, measured over a 72-hour treatment period, referenced to either untreated MIA-PACa-2 cell control ("Untreated/empty fibre") or untreated PANC-1 cell control ("Untreated/empty fibre") as appropriate.

FIG. 20 shows a flow-cytometric cell cycle analysis using Vybrant™ DyeCycle™ Violet Stain DNA staining of A) MIA-PaCa-2 cells and B) PANC-1 cells. The histograms shown in FIG. 20 show the free drug (gemcitabine or paclitaxel) and the drug eluted from the correlating coaxial fibre 120 as overlapping graphs.

Figure 18:
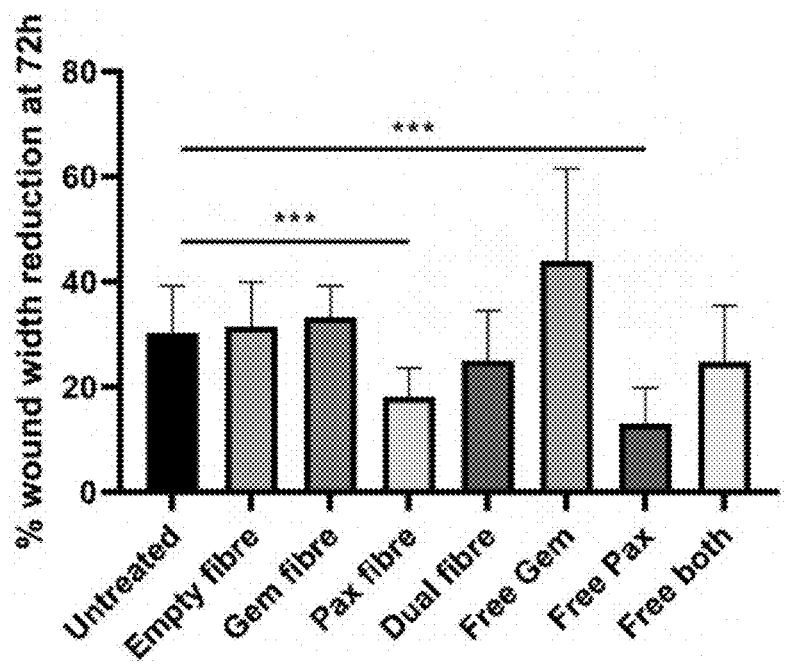
FIG. 18 shows a plot that reveals the reduction (%) in width of a wound over a 72-hour treatment period following exposure to a coaxial fibre without any preloaded drugs ("Empty fibre"), a coaxial fibre loaded with gemcitabine ("Gem fibre"), a coaxial fibre loaded with paclitaxel ("Pax fibre"), and a coaxial fibre loaded with both gemcitabine and paclitaxel ("Dual fibre"), when compared to a series of controls including: untreated MIA-PACa-2 cell control ("Untreated"), free gemcitabine ("Free Gem"), free paclitaxel ("Free Pax"), and a combination of free gemcitabine and free paclitaxel ("Free both")
Figure 19:
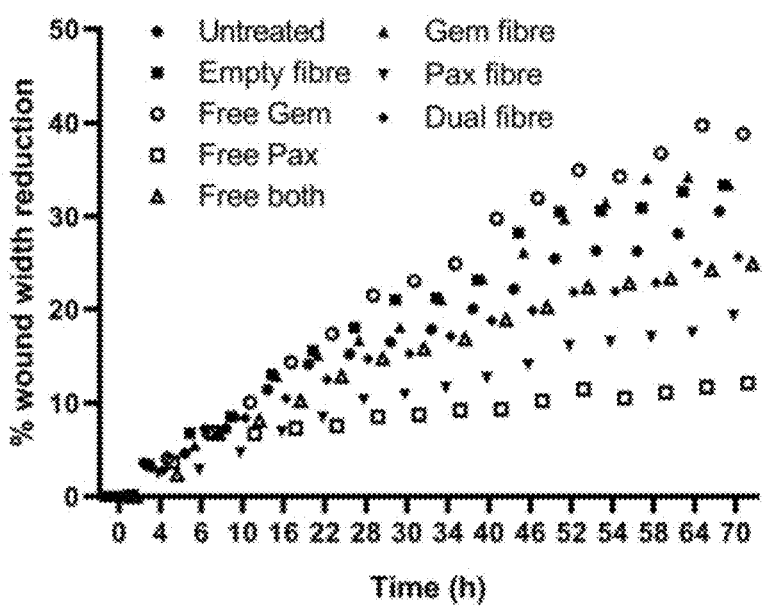
FIG. 19 shows a plot that reveals the reduction (%) in width of a wound over a 72-hour treatment period following exposure to a coaxial fibre without any preloaded drugs ("Empty fibre"), a coaxial fibre loaded with gemcitabine ("Gem fibre"), a coaxial fibre loaded with paclitaxel ("Pax fibre"), and a coaxial fibre loaded with both gemcitabine and paclitaxel ("Dual fibre"), when compared to a series of controls including: untreated MIA-PACa-2 cell control ("Untreated"), free gemcitabine ("Free Gem"), free paclitaxel ("Free Pax"), and a combination of free gemcitabine and free paclitaxel ("Free both")

Like the observations made in respect of the cell migration studies in FIGS. 17 to 19 above, when the drugs (gemcitabine and/or paclitaxel) are eluted from a coaxial fibre 120 preloaded with one or both drugs, the cell cycle analysis data shown in FIG. 20 clearly indicates that there is no significant difference between this data and that of the free drugs themselves, which again points to bioequivalence.

Figure 21:
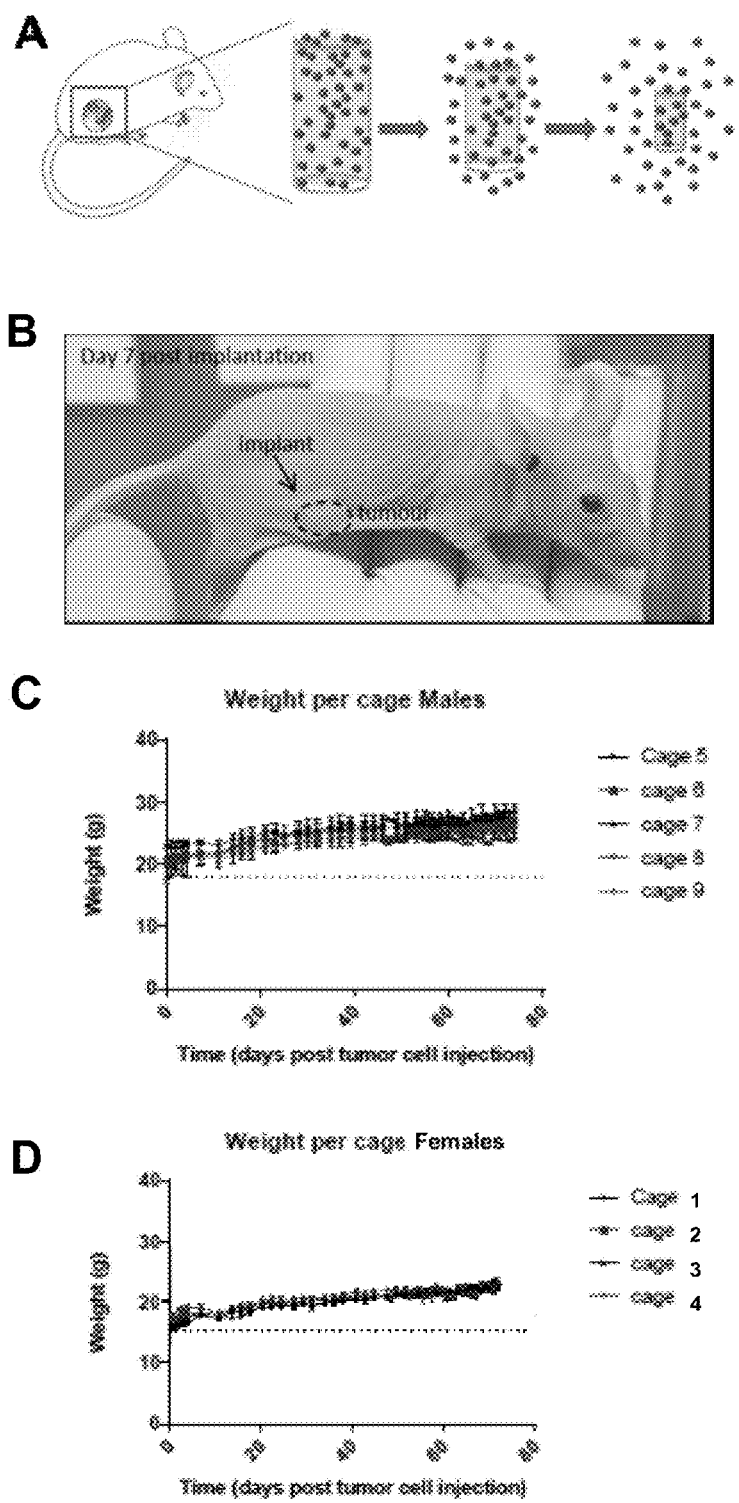
FIG. 21 shows A) a schematic representation of the in vivo drug release mechanism associated with a coaxial fibre implant loaded with one or more drugs (gemcitabine, paclitaxel), B) a photograph of a mouse implanted with a coaxial fibre implantable device 7 days after implantation (the arrow indicates the placement of the coaxial fibre implant, the circle indicates the presence of a tumour), C) a plot that reveals the average weight change (g) in male mice (Cages 5-9), indicating no toxicity, and D) a plot that reveals the average weight change (g) in female mice (Cages 1-4), indicating no toxicity after implantation with either drug-loaded or non-drug loaded coaxial fibre implant.

FIG. 21 shows A) a schematic representation of the in vivo drug release mechanism associated with a coaxial fibre implant 110 loaded with one or more drugs (gemcitabine, paclitaxel), while B) shows a photograph of a pancreatic cancer xenograft mouse, in which an empty coaxial fibre implant 110 has been implanted subcutaneously into the mouse at the location (indicated by the arrow) of a tumour (see dashed circle).

As shown in FIG. 21, plot C) reveals that the average weight change (g) in male mice (post tumour cell injection) injected with a coaxial fibre implant 110 loaded with both gemcitabine and paclitaxel, showed no weight loss, no implant migration, and no adverse effects over a period of around 80 days. These results clearly indicate that the coaxial fibre implant 110 exhibits no toxicity toward male mice.

Similarly, and as shown in FIG. 21, plot D) reveals that the average weight change (g) in female mice (post tumour cell injection) injected with a coaxial fibre implant 110 loaded with both gemcitabine and paclitaxel, showed no weight loss, no implant migration, and no adverse effects over a period of around 80 days, which again, clearly indicates that the coaxial fibre implant 110 exhibits no toxicity toward female mice.

Figure 22:
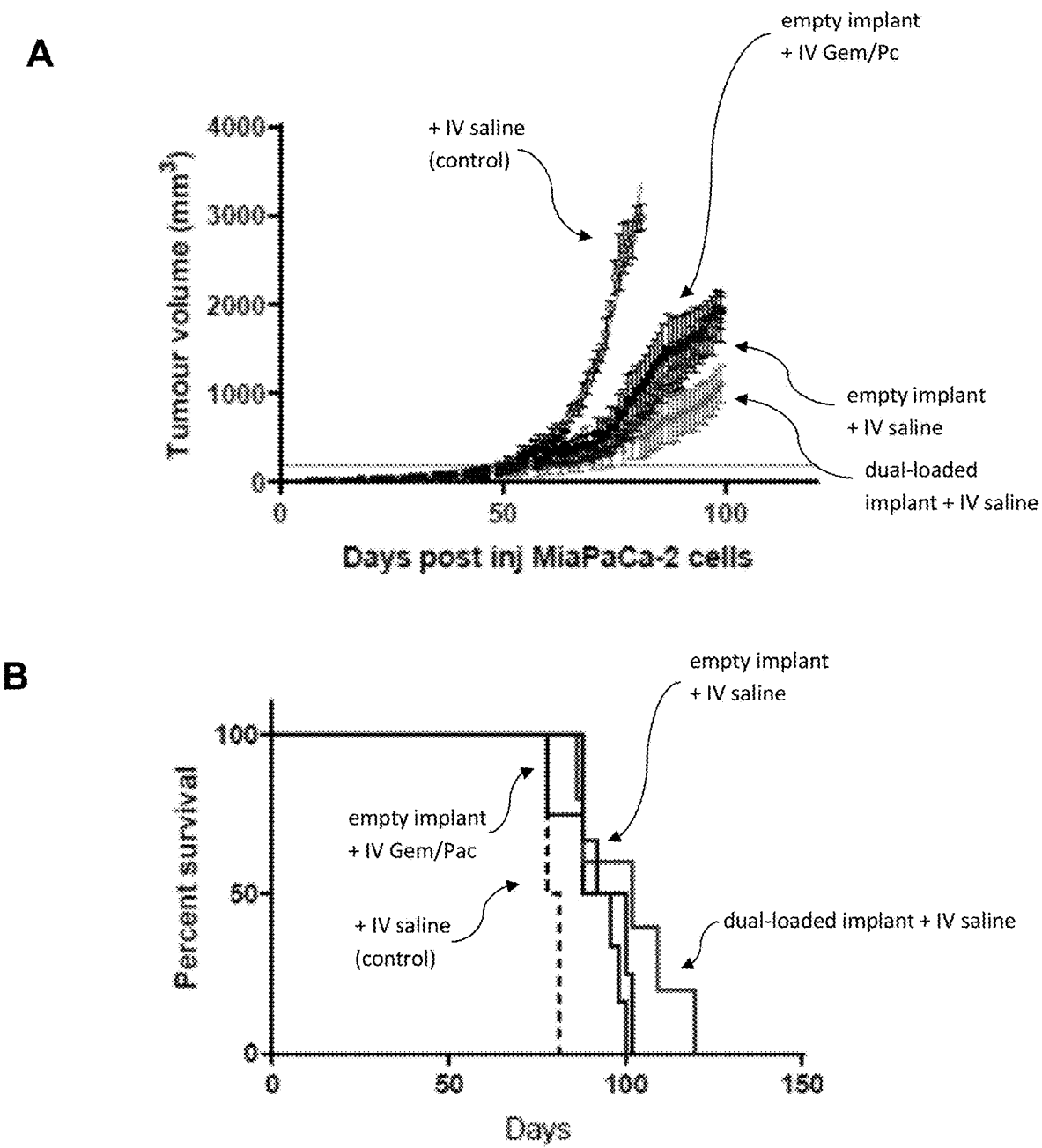
FIG. 22 shows A) a plot that reveals the impact on the volume (mm$^3$) of tumours in mice bearing a coaxial fibre implant loaded with both gemcitabine and paclitaxel ("dual-loaded implant+IV saline") following injection of MIA-PaCa-2 cells measured over a period of 100 days, when compared to a series of controls including: an intravenous (IV) saline (control), an empty coaxial fibre implant+IV saline (control), and an empty coaxial fibre implant+IV gemcitabine and paclitaxel (control); and B) a Kaplan Meir survival curve showing the increased survival rate (%) of mice bearing a coaxial fibre implant loaded with both gemcitabine and paclitaxel ("dual-loaded implant+IV saline") measured over a period of 150 days, when compared to a series of controls including: an IV saline (control), an empty coaxial fibre implant+IV saline (control), and an empty coaxial fibre implant+IV gemcitabine and paclitaxel (control)

As shown in FIG. 22, plot A) reveals that the volume ($mm^3$) of tumours in mice (post MIA-PaCa-2 tumour cell injection) injected with a coaxial fibre implant 110 loaded with both gemcitabine and paclitaxel showed minimal increase when compared to the controls.

While, as shown in FIG. 22, plot B) reveals that mice that have been injected with a coaxial fibre implant 110 loaded with both gemcitabine and paclitaxel showed an increased survival rate when compared to the controls.

Figure 23:
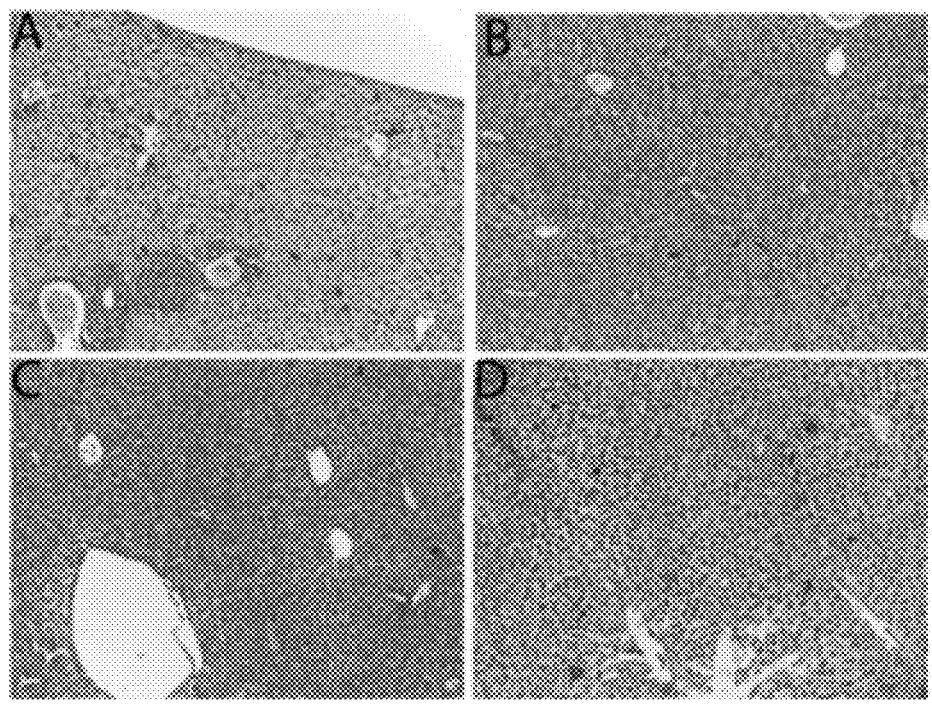
FIG. 23 shows photographs of a series of liver samples stained with H&E (Haematoxylin and Eosin) that have been taken from a cohort of mice bearing D) a coaxial fibre implant loaded with both gemcitabine and paclitaxel ("dual-loaded implant+IV saline"), when compared to a series of controls including: A) an intravenous (IV) saline (control), B) an empty coaxial fibre implant+IV saline (control), C) an empty coaxial fibre implant+IV gemcitabine and paclitaxel (control)

As shown in FIG. 23, the photograph D) of a liver sample stained with H&E (Haematoxylin and Eosin) that has been taken from a cohort of mice injected with a coaxial fibre implant 110 loaded with both gemcitabine and paclitaxel, reveals no metastatic lesions or no toxicity from the implants, when compared to the photographs associated with the controls.

Figure 24:
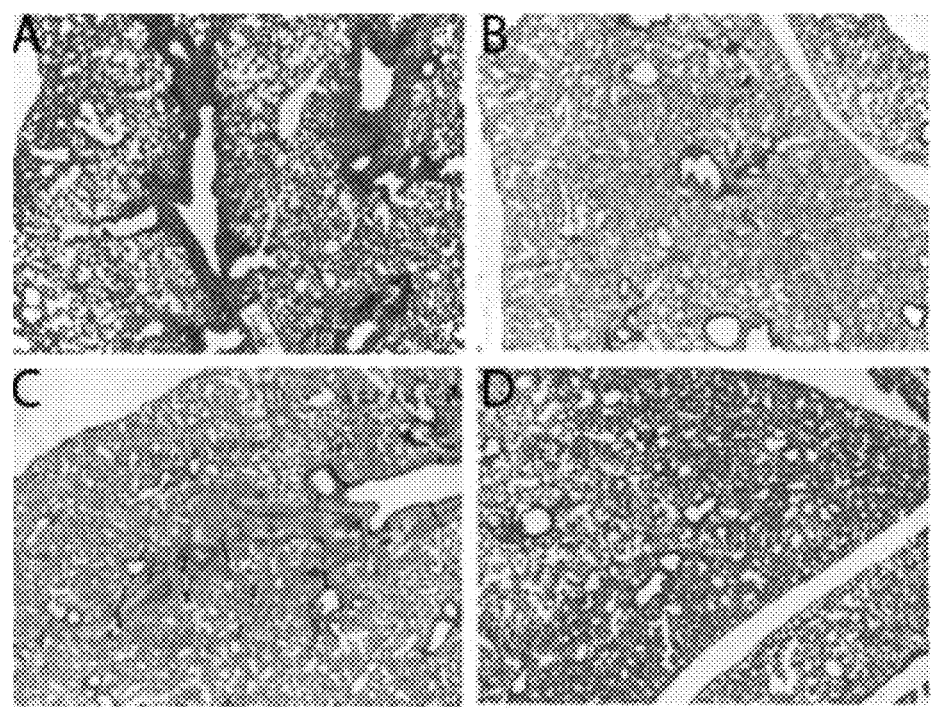
FIG. 24 shows photographs of a series of lung samples stained with H&E (Haematoxylin and Eosin) that have been taken from a cohort of mice bearing D) a coaxial fibre implant loaded with both gemcitabine and paclitaxel, when compared to a series of controls including: A) an intravenous (IV) saline (control); B) an empty coaxial fibre implant+IV saline (control), and C) an empty coaxial fibre implant+IV gemcitabine and paclitaxel (control)

As shown in FIG. 24, the photograph D) of a lung sample stained with H&E (Haematoxylin and Eosin) that has been taken from a cohort of mice injected with a coaxial fibre implant 110 loaded with both gemcitabine and paclitaxel, reveals no metastatic lesions, when compared to the photographs associated with the controls. This result also indicates that the dual-loaded coaxial fibre implant 110 shows no toxicity towards the mice.

Figure 25:
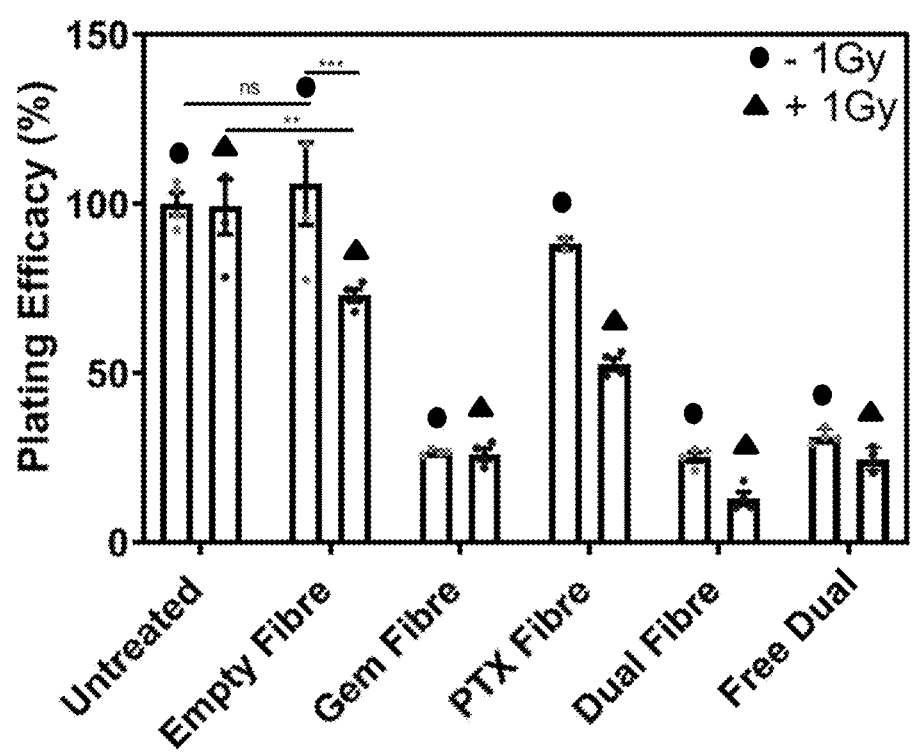
FIG. 25 shows a clonogenic survival assay that reveals the plating efficacy (%) of a coaxial fibre implant loaded with both gemcitabine and paclitaxel ("Dual Fibre"), when compared to a coaxial fibre loaded with gemcitabine ("Gem Fibre") and a coaxial fibre loaded with paclitaxel ("PTX fibre"), as well as to series of controls including a combination of free gemcitabine and free paclitaxel ("Free Dual") and an empty coaxial fibre implant ("Empty Fibre"), when measured either with (circle) or without (triangle) exposure to 1 Gy radiation. Surviving fractions were normalized to an untreated control ("Untreated"). Data points are the mean of quadruplicate values±SD. ns=$P>0.05$, =$P<0.01$, *=$P<0.001$, ****=$P<0.0001$.

As shown in FIG. 25, the clonogenic survival assay reveals that when the study is undertaken in combination with 1 Gy radiation, the coaxial fibre implant 110 loaded with both gemcitabine (0.5 μm) and paclitaxel (0.15 μm) shows the greatest efficacy as a radiosensitiser, when compared to the controls. Notably, the inventors found that the empty coaxial fibre also showed a radio-sensitising effect.

Figure 26:
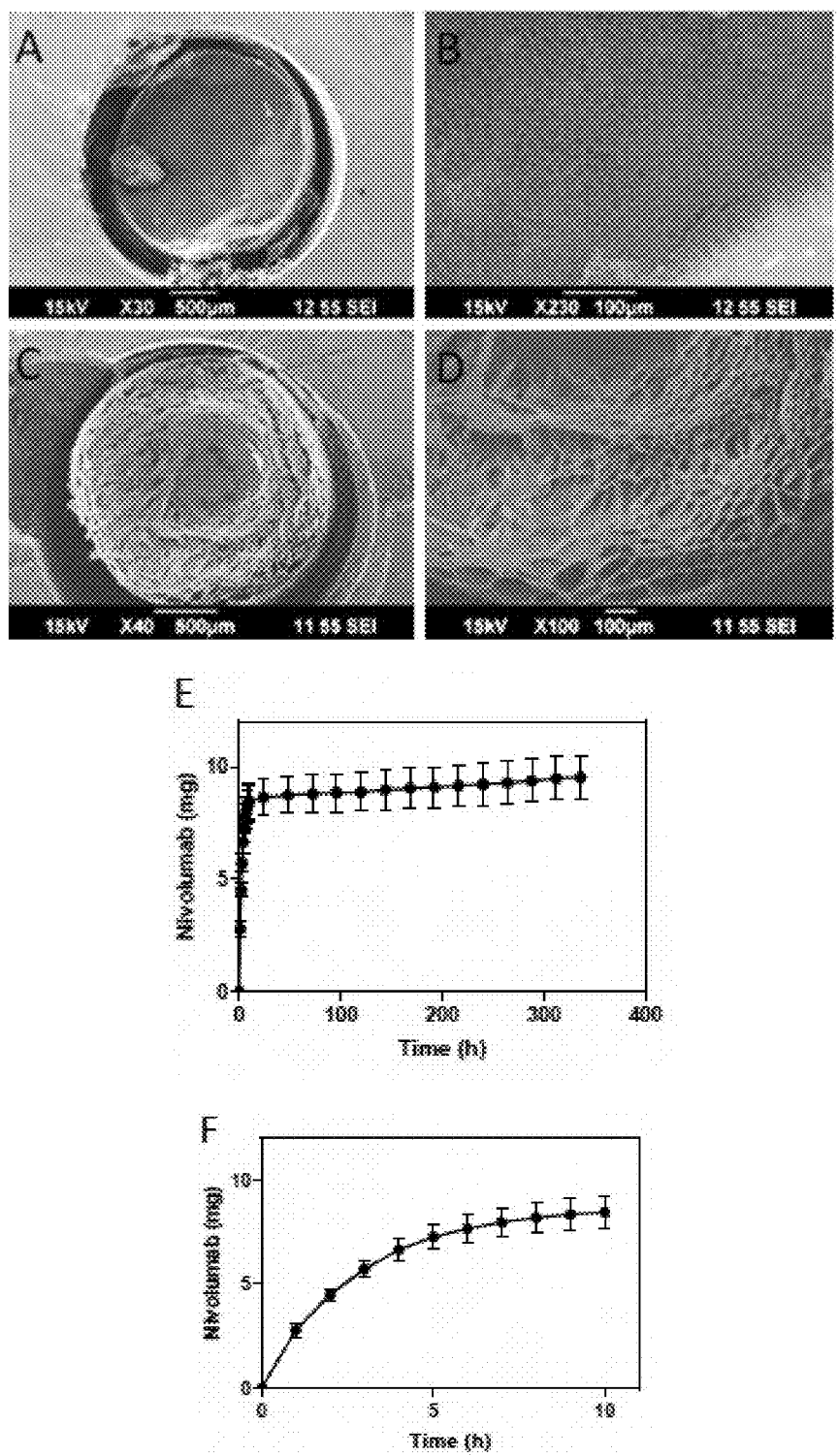
FIG. 26 shows scanning electron microscopy (SEM) images of cross sections of the alginate (Alg) core of a coaxial fibre implant taken before (A, B) and after (C, D) loading with nivolumab (A, C—Scale: 500 μm, B, D—Scale: 100 μm), and plots revealing the amount (mg) of nivolumab released from the fibre implant over C) a 14 day period, and D) the first 10 hour period. Values are the mean (±SEM) n=6.

FIG. 26 shows scanning electron microscopy (SEM) images of cross sections of the alginate (Alg) core of a coaxial fibre implant 110 taken before (A, B) and after (C, D) loading with the hydrophilic drug, nivolumab. The SEM images clearly reveal the change in porosity observed following the addition of nivolumab.

As also shown in FIG. 26, the two plots reveal the amount (mg) of nivolumab that is released from the alginate (Alg) core of the coaxial fibre implant 110 over C) a 14-day period, and D) the first 10-hour period. These results clearly show that there is an initial burst release of nivolumab during the first 10 hours followed by a sustained release over the next 300 or so hours.

Figure 27:
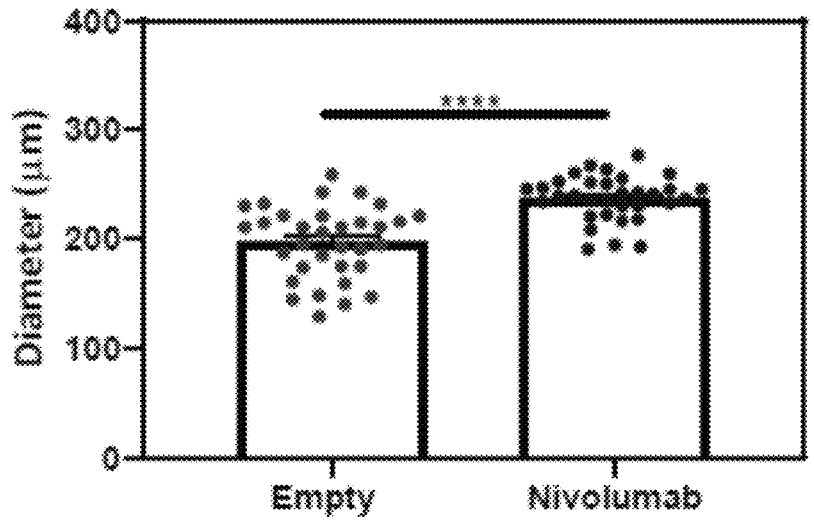
FIG. 27 shows a plot that reveals the diameter (μm) of the alginate (Alg) core of a coaxial fibres produced using a wet spinning technique (measured after drying) with a fibre without any preloaded drugs ("Empty"), a coaxial fibre loaded with nivolumab ("Nivolumab"). The bars represent the mean of n=33 measurements±SEM.

As shown in FIG. 27, the plot reveals that the diameter (μm) of the alginate (Alg) core of the coaxial fibre implant 110 has increased after being loaded with nivolumab.

TABLE 2

| Theoretical Loading (mg/m) | Actual Loading (mg/m) | Encapsulation Efficiency (%) |
|---|---|---|
| 15.37 | 9.51 | 62.16 |

Table 2 shows the drug loading and encapsulation efficacy (%) of the alginate (Alg) core of the coaxial fibre implant 110 on loading with nivolumab, as determined through complete release of drug and quantification using HPLC.

To study the activity (%) of nivolumab eluted from the alginate (Alg) core of a coaxial fibre implant 110, PD-L1 aAPC/CHO-K1 cells were plated and incubated at 37° C. for 16 to 20 hours prior to the addition of increasing concentrations of nivolumab and PD-1 Effector Cells. After 6 hours, Bio-Glo™ Reagent was added to the plated cells and the luminescence was measured using a GloMax™ Discover System.

Figure 28:
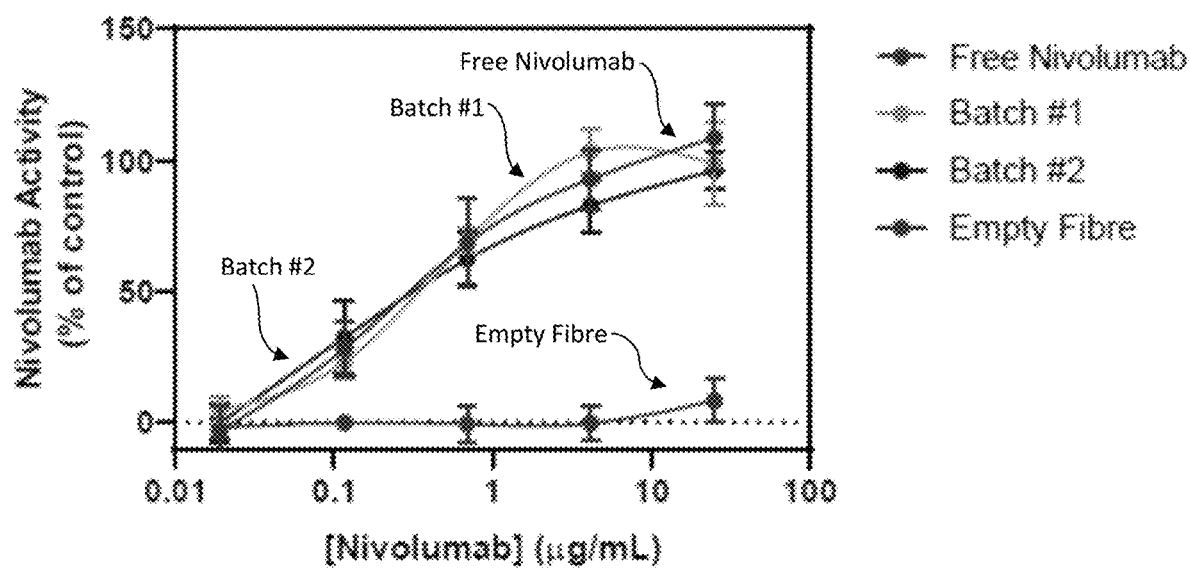
FIG. 28 shows a plot that reveals the activity (% of untreated control) of nivolumab eluted from the alginate (Alg) core of a coaxial fibre implant ("Batches #1 and #2"), when compared to the activity of free nivolumab ("Free Nivolumab") and an empty fibre implant ("Empty Fibre"), as references.

The results from the study, as shown in FIG. 28, reveal that the activity (%) of the nivolumab eluted from the alginate (Alg) core of the coaxial fibre implant 110, when compared to the activity of (i) free nivolumab and (ii) an empty fibre implant, as references, is sufficiently retained following elution from the alginate (Alg) core of the coaxial fibre implant 110.

Figure 29:
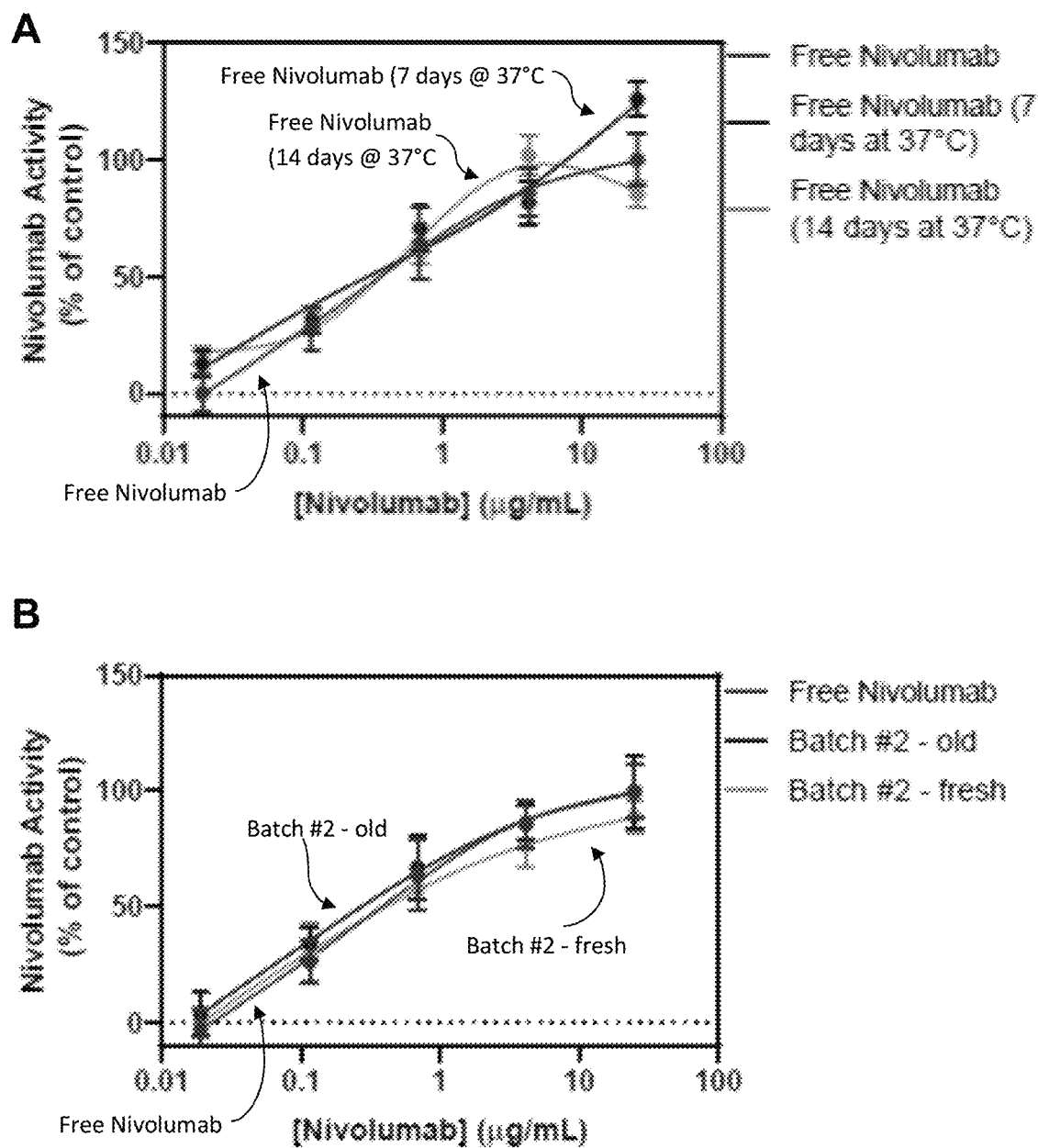
FIG. 29 shows a plot that reveals the activity (% of untreated control) of A) free nivolumab ("Free Nivolumab"), following storage for 7 days at 37° C. and 14 days at 37° C., and B) nivolumab eluted from an old batch ("Batch #2—old") and a fresh batch ("Batch #2—fresh") of a coaxial fibre implant loaded with nivolumab, when compared to the activity of free nivolumab ("Free Nivolumab"), as a reference.

In addition, and as shown in FIG. 29, the activity (%) of the nivolumab eluted from the alginate (Alg) core of the coaxial fibre implant 110 is not affected by the release conditions, nor is it affected by short term storage.

Advantages

The implantable devices 10, 110 and method for implanting said devices 10, 110 in a subject for use in treating a medical condition provide a number of benefits, including, but not limited to:

[1]. The coaxial fibres 20, 120 can be loaded with two drugs simultaneously (for example, gemcitabine and paclitaxel) to target a cancerous tumour in a synergistic manner.

[2]. An enhanced drug uptake and efficacy due to the fact that the implantable devices 10, 110 can be implanted locally (directly at the site of the tumour), thereby offering a strategic and precise spatial control that significantly reduces the required systemically administered drug dosage and often the side/off-target effects.

[3]. Temporal control over the release profile of the drugs preloaded into the polymers forming the coaxial fibres 20, 120 to maintain therapeutic concentrations over a longer duration of time.

[4]. Greater protection of the pre-loaded drugs from degradation or clearance until they are released in vivo.

[5]. The coaxial fibres 20, 120 can either be cut into small pieces and used to form the corresponding implantable device 10, 110 that is injected into a tumour via ultrasound-guided endoscopic implantation as described above, or via transdermal intralesional injection for palpable primary or secondary tumours or via CT-scan or ultrasound guided intra-visceral injection or it can be post-processed via textile engineering techniques (such as weaving or braiding) to make an implantable device in the form of a patch (not shown) for applying directly to a tumour.

Materials and Methods

Chemicals, Solvents and Reagents

Sodium alginate, polycaprolactone (PCL), calcium chloride ($CaCl_2$)), calcium carbonate ($CaCO_3$), sodium hydroxide (NaOH), glucono delta-lactone (GDL) and acetic acid were purchased from Sigma-Aldrich Co. USA. Gemcitabine hydrochloride was purchased from Toronto Research Chemicals, CA. Paclitaxel was purchased from FocusBio, Australia. Simulated biological fluid (SBF) was prepared using analytical grade reagents consisting of 5.403 g $l^{-1}$ NaCl, 0.504 g $l^{-1}$ $NaHCO_3$, 0.426 g $l^{-1}$ $NaCO_3$, 0.225 g $l^{-1}$ KCl, 0.230 g $l^{-1}$ $K_2HPO_4.3H_2O$, 0.311 g $l^{-1}$ $MgCl_2.6H_2O$, 0.8 g $l^{-1}$ NaOH, 0.293 g $l^{-1}$ $CaCl_2$, 0.072 g $l^{-1}$ $Na_2SO_4$ and 17.892 g $l^{-1}$ HEPES as buffering agent. The pH was adjusted to 7.40±0.05 using 1.0 M NaOH solution. The CellTiter 96® Aqueous One Solution Cell Proliferation Assay (MTS) was from purchased from Promega, Australia. DMEM-High glucose media and foetal calf serum (FCS) were purchased from Invitrogen, USA. Trypsin/EDTA was purchased from Life Technologies, Australia. Dimethylformamide (DMF) was purchased from RCI Labscan (Thailand).

Spinning Solutions

Alginate solution was prepared by using an optimised internal ionic crosslinking method.[4, 5] Firstly, 15 mM $CaCO_3$ was added to water, before adding alginate powder to a final concentration of 3% w/v. In gemcitabine loaded solutions, the gemcitabine was added at a final concentration of 50 mM to water, before adjusting the solution to pH7, then $CaCO_3$ and alginate were added and stirred overnight. Immediately before spinning, GDL was added to a final concentration of 30 mM and stirred to dissolve. PCL was prepared at a concentration of 15% w/v by adding PCL pellets to DMF while stirring at 70° C. and mixed overnight. Paclitaxel was added to PCL solution at RT to give a final concentration of 15 mM.

Wet Spinning of Fibres

Fibres were prepared according to a literature method.[6] Briefly, the spinning solutions were placed in 10 mL syringes and placed in a programmable syringe pump (kd-Scientific KDS100). Coaxial fibres 20, 120 were spun using a novel coaxial spinneret with two input ports. Both the shell material (PCL) and the core material (alginate) were extruded at 50 mL/h into a bath containing 2% w/v $CaCl_2$), and collected from the coagulation bath on a rotating mandrel at a fibre formation rate of 65 cm/min.

Fibre Characterisation

Morphology

Scanning electron microscopy (SEM) was used to observe the internal morphology of hydrated fibres. Individual hydrated coaxial fibres 20, 120 were placed into holes drilled into the surface of a brass block such that the fibres 20, 120 protruded approximately 1-2 mm above the surface. The block was then plunged into liquid nitrogen for approximately 45 sec and a liquid nitrogen cooled blade run over the surface of the block to obtain a cross section of the fibres 20, 120. The block was then quickly transferred to the SEM (JEOL 6490LV SEM) for imaging. Secondary electron images were taken at 15 kV operating voltage. No coating of the fibres 20, 120 was required, as they remained conductive in the SEM vacuum for approximately 20 minutes due to their high water content.

Fibre Diameter

Fibre diameter was measured using inverted light microscopy, by measuring at nine locations along a 1 cm length, with a total of four lengths of fibre 20, 120 measured. Images were taking using a Motic digital microscope camera and diameter calculated using Moti Images 2.0 (Motic China Group).

Drug Loading

The actual loading of drug was determined by performing a drug release experiment with the endpoint defined by no further release and measured using high performance liquid chromatography (HPLC).

Drug Release 30 cm of each coaxial fibre 20, 120 was placed in a 2 mL Eppendorf tube in triplicate. The release medium for paclitaxel release contained PBS, containing 2.4% (w/w) Tween-80 and 4% (w/w) Kolliphor EL. The release medium for gemcitabine contained SBF, containing $10^4$ U·L lipase and 1× Penicillin/Streptomycin. 1.5 mL of release medium was added to each tube, and incubated at 37° C. At each specified timepoint, the medium was removed and replaced with fresh medium. The amount of drug released from gemcitabine loaded fibres was assessed using Shimadzu HPLC system comprising of a UV-Vis detector (SPD-10AV), system controller (SCL-10A), auto injector (SIL-10AD), Liquid chromatograph (LC-10AT) and degasser (DGU-14A).

All samples were filtered through a 0.22 µm syringe membrane filter prior to injection. Chromatographic analysis of gemcitabine was carried out using a mobile phase of ultra-pure water and ACN at a ratio of 95:5 using an isocratic elution. Injection volume was 10 µL on to a Grace C18 column (4.6×250 mm, 5 µm particle size) at a flow rate of 1 mL/min. Gemcitabine was detected by the UV-VIS detector at 272 nm.

A standard curve was prepared using gemcitabine concentrations ranging from 0.004 to 0.5 mg/mL. Paclitaxel detection was carried out at 272 nm using a mobile phase of ultra-pure water and ACN using gradient elution according to the following program: from 0 to 30 min, linear gradient of 50% to 100% ACN. From 30-38 min, hold at 100% ACN. From 38-40 min, linear gradient from 100% to 50% ACN, followed by 40 to 60 min at 50% ACN. The injection volume was 10 µL and flow rate was 1 mL/min. Mobile phase for both separations was prepared daily and filtered and degassed using an ultra-sonicating water bath. Data acquisition was carried out using Class-VP software (V. 6.14 SP1).

Echogenicity

1 OD 10 nm gold nanoparticles (AuNP) were mixed with the alginate solution prior to spinning at a concentration of $2.8 \times 10^{12}$ particles/mL. Coaxial fibres 20, 120 were fabricated with the AuNP alginate in the core, and PCL solution for the shell. Fibres 20, 120 were threaded through an ultrasound training model, and imaged using a clinical ultrasound machine.

Cell Lines and Culture Conditions

The MIA-PaCa-2 and PANC-1 human PDAC cell lines were purchased from the ATCC. All cell lines were authenticated using short tandem repeat (STR) profiling at the Garvin Institute of Medical Research. Cells were confirmed to be mycoplasma free. All cells were cultured in DMEM-high glucose media supplemented with 10% foetal calf serum (FCS) at 37° C., 95% humidity, and 5% $CO_2$ in a Heracell incubator (Kendor Laboratory Products, Germany).

Growth Inhibition

Cell monolayers were generated as previously described.[7] PANC-1 or MIA-PaCa-2 cells were seeded at 5000 cell/well in complete media (200 µL) containing 1× penicillin/streptomycin in 96-well flat-bottomed plates 24 h prior to addition of fibres 20 (devoid of drugs, gemcitabine, paclitaxel, or dual loaded with gemcitabine and paclitaxel) (0.5 cm). Each fibre length was heat sealed at each end to prevent core from dissociating. Images were taken using the IncuCyte ZOOM real-time quantitative live-cell imaging system (Essen Bioscience, USA) at 10× magnification. Cell viability was assessed at 24, 48 and 72 h using the colorimetric MTS assay according to manufactures instructions. Briefly, at the end time point, fibre lengths were removed from each well and 20 µL MTS reagent added and incubated for 3 h at 37° C. before being analysed using UV-Vis at 490 nm.

Inhibition of Tumour Spheroid Growth

KPC cells were seeded at 100 cell/well in a final volume of 200 µL in Corning Costar ultra-low attachment U-bottomed plates. Spheroids spontaneously formed 4 days post seeding. Empty, paclitaxel, gemcitabine or dual loaded fibres were heat sealed and added (0.5 cm). Spheroids were imaged daily for 5 days using fluorescence microscope, and spheroid diameter measured using Image J software. All images were acquired at 10× magnification.

Organotypic Assays

Collagen matrices were formed as described in the literature.[8] Briefly, collagen I was extracted from rat tails, and matrices formed by mixing TIFs with a neutral collagen solution. 50 pre-established PANC-1 tumour spheroids (seeded at 350 cell/well 8 days prior) were embedded in each matrix, and matrices allowed to contract over a period of 7 days, refreshing the media when necessary. A 5 cm length of fibre (empty or dual drug loaded) was then placed on top of each matrix, ensuring the media is covering both and incubated for 5 days before histological analysis was performed.

Histological Analysis

Histological analysis was performed as described in the literature.[9] Briefly, samples were fixed in 10% formalin and processed using the Leica Felons Dual Retort tissue processer. Histological staining was performed on 5 µm sections, deparaffinised in xylene and rehydrated using graded ethanol washes. Haematoxylin and eosin, and picrosirius red staining was performed on a Lecia Autostainer XL. Images were taken using a Leica light microscope.

REFERENCES

[1]. Indolfi, L., et al., *A tunable delivery platform to provide local chemotherapy for pancreatic ductal adenocarcinoma.* Biomaterials, 2016. 93: p. 71-82.

[2]. Yi, H.-G., et al., *A 3D-printed local drug delivery patch for pancreatic cancer growth suppression*. Journal of Controlled Release, 2016. 238: p. 231-241.
[3]. Jimim Han et al., *Endoscopic ultrasound-guided direct intervention for solid pancreatic tumours*, Clin. Endosc., 2017, 50, p. 126-137.
[4]. Jang, J., et al., *Effects of alginate hydrogel cross-linking density on mechanical and biological behaviors for tissue engineering*. Journal of the Mechanical Behavior of Biomedical Materials, 2014. 37: p. 69-77.
[5]. Kuo, C. K. and P. X. Ma, *Ionically crosslinked alginate hydrogels as scaffolds for tissue engineering: Part 1. Structure, gelation rate and mechanical properties*. Biomaterials, 2001. 22(6): p. 511-521.
[6]. Mirabedini, A., et al., *Development and characterization of novel hybrid hydrogel fibers*. Macromolecular Materials and Engineering, 2015. 300(12): p. 1217-1225.
[7]. Wade, S. J., et al., *Preparation and in vitro assessment of wet-spun gemcitabine-loaded polymeric fibers: Towards localized drug delivery for the treatment of pancreatic cancer*. Pancreatology, 2017.
[8]. Timpson, P., et al., *Organotypic Collagen I Assay: A Malleable Platform to Assess Cell Behaviour in a 3-Dimensional Context*. Journal of Visualized Experiments: JoVE, 2011(56): p. 3089.
[9]. Harris, N. L. E., et al., *SerpinB2 regulates stromal remodelling and local invasion in pancreatic cancer*. Oncogene, 2017. 36: p. 4288.

Definitions

Whenever a range is given in the specification, for example, a temperature range, a time range, or concentration range, all intermediate ranges and subranges, as well as all individual values included in the ranges given are intended to be included in the disclosure. It will be understood that any subranges or individual values in a range or subrange that are included in the description herein can be excluded from the claims herein.

All definitions, as defined and used herein, should be understood to control over dictionary definitions, definitions in documents incorporated by reference, and/or ordinary meanings of the defined terms.

Throughout this application, the term "about" is used to indicate that a value includes the inherent variation of error for the device, the method being employed to determine the value, or the variation that exists among the study subjects.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Spatially relative terms, such as "inner," "outer," "beneath," "below," "lower," "above," "upper," and the like, may be used herein for ease of description to describe one element or feature's relationship to another element(s) or feature(s) as illustrated in the Figures. Spatially relative terms may be intended to encompass different orientations of the device in use or operation in addition to the orientation depicted in the Figures.

While the invention has been described in conjunction with a limited number of embodiments, it will be appreciated by those skilled in the art that many alternatives, modifications and variations in light of the foregoing description are possible. Accordingly, the present invention is intended to embrace all such alternatives, modifications and variations as may fall within the spirit and scope of the invention as disclosed.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

The claims defining this invention are as follows:

1. An injectable implantable device used in treating a medical condition when implanted into a subject, the device comprising:
   at least one coaxially extruded fibre of a hydrophilic polymer and a hydrophobic polymer, wherein at least one of said polymers is loaded with an agent that is active towards treating the medical condition,
   a sheath encapsulating the at least one coaxially extruded fiber substantially therein for protecting the at least one coaxially extruded fiber during implantation by injection and controlling release of the active agent from the at least one coaxially extruded fiber, wherein the sheath comprises a plurality of apertures disposed along the length of the sheath in a spaced apart arrangement, and
   an echogenic locating means for use in locating the implantable device when implanted into a subject.

2. The device of claim 1, wherein the sheath is formed from a polymer selected from the group consisting of polycaprolactone, poly(lactic acid), poly(lactic-co-glycolic acid), poly(propylene glycol) and a poly(l-amino acid).

3. The device of claim 1, wherein one or more of the plurality of apertures has a diameter of about 100 μm.

4. The device of claim 1, wherein the echogenic locating means comprises (i) a metal coating formed on an external surface of at least one of the hydrophilic polymer and the hydrophobic polymer of the at least one coaxially extruded fibre, or (ii) a plurality of metal nanoparticles embedded substantially within at least one of the hydrophilic polymer and the hydrophobic polymer of the at least one coaxially extruded fibre, or (iii) a metal coating deposited on an external surface of the sheath.

5. The device of claim 1, wherein the active agent is a hydrophilic drug loaded into the hydrophilic polymer and/or wherein the active agent is a hydrophobic drug loaded into the hydrophobic polymer and/or wherein each of said hydrophilic polymer and said hydrophobic polymer is loaded with an agent that is active towards treating the medical condition.

6. The device of claim 1 wherein a hydrophilic polymer is comprised in a core of the at least one coaxially extruded fibre and a hydrophobic polymer is comprised in a shell that surrounds the hydrophilic polymer core of the at least one coaxially extruded fibre, or wherein a hydrophobic polymer is comprised in a core of the at least one coaxially extruded fibre and a hydrophilic polymer is comprised in a shell that surrounds the hydrophobic polymer core of the at least one coaxially extruded fibre.

7. The device of claim 5, wherein the hydrophobic polymer is selected from the group consisting of: polycaprolactone, poly(lactic acid), poly(lactic-co-glycolic acid), poly(2-oxazoline), polyglycerol sebacate, poly(propylene glycol and a poly(l-amino acid) and/or wherein the hydrophilic polymer is selected from the group consisting of: alginate, chitosan, carboxymethyl cellulose, poly(vinyl alcohol), hyaluronic acid and poly(ethylene glycol).

8. The device of claim 5, wherein the hydrophobic polymer is polycaprolactone and the hydrophilic polymer is alginate.

9. The device of claim 1 wherein the active agent is selected from the group consisting of: a chemotherapeutic agent, a biologic, an immune modulating agent, a radioactive or radioisotope material, a contrast agent or fluorescent dye, a steroid, a fatty acid, a vitamin, and any combination thereof.

10. The device of claim 5, wherein the hydrophobic drug is selected from the group consisting of: paclitaxel, camptothecan, everolimus, epothilone, curcumin, docetaxel, and any combination thereof.

11. The device of claim 5, wherein the hydrophilic drug is selected from the group consisting of: gemcitabine, a platinum agent, 5-fluorouracil, irinotecan, a taxane, cyclophosphamide, rituximab, cetuximab, trastuzumab, pertuzumab, sunitinib, bevacizumab, an anti-EGFR molecule, an anti-CTLA4 antibody, an anti-PD1 including nivolumab, or anti-PDL1 antibody or inhibitor, tisagenlecleucel, an immune modulating agent, and any combination thereof.

12. The device of claim 1, wherein the medical condition to be treated is cancer and the hydrophilic polymer is alginate loaded with gemcitabine and the hydrophobic polymer is polycaprolactone loaded with paclitaxel.

13. The device of claim 12, wherein the amount of gemcitabine loaded into the hydrophilic alginate is in the range from about 1.2% to 1.5% by weight.

14. The device of claim 12, wherein the amount of paclitaxel loaded into the hydrophobic polycaprolactone in the range from about 1.2% to 1.5% by weight.

15. The device of claim 1, wherein the at least one coaxially extruded fibre is formed using a method selected from the group consisting of: wet spinning, electrospinning, coaxial melt extrusion printing, coaxial melt electro-writing, hot melt extrusion and pulsatile fibre spinning.

16. A method of delivering at least one active agent to a subject, the method comprising:
    implanting an injectable implantable device according to claim 1 into a subject presenting a medical condition that is treatable with the at least one active agent.

17. The method of claim 16, wherein implanting is carried out using endoscopic ultrasound-guided implantation.

* * * * *